US009089274B2

(12) United States Patent
Wu et al.

(10) Patent No.: US 9,089,274 B2
(45) Date of Patent: Jul. 28, 2015

(54) DENOISE MCG MEASUREMENTS

(75) Inventors: Chenyu Wu, Mountain View, CA (US); Jing Xiao, Cupertino, CA (US)

(73) Assignee: Seiko Epson Corporation, Tokyo (JP)

( * ) Notice: Subject to any disclaimer, the term of this patent is extended or adjusted under 35 U.S.C. 154(b) by 979 days.

(21) Appl. No.: 13/239,997

(22) Filed: Sep. 22, 2011

(65) Prior Publication Data
US 2013/0079622 A1 Mar. 28, 2013

(51) Int. Cl.
*A61B 5/05* (2006.01)
*A61B 5/00* (2006.01)
*A61B 5/04* (2006.01)

(52) U.S. Cl.
CPC ............... *A61B 5/05* (2013.01); *A61B 5/0044* (2013.01); *A61B 5/04007* (2013.01); *A61B 5/04005* (2013.01); *A61B 2562/046* (2013.01)

(58) Field of Classification Search
CPC .... A61B 5/05; A61B 5/0044; A61B 5/04007; A61B 2562/046; A61B 5/04005
USPC .................................................. 600/407, 409
See application file for complete search history.

(56) References Cited

U.S. PATENT DOCUMENTS

| 5,117,834 | A * | 6/1992 | Kroll et al. .................. 600/518 |
|---|---|---|---|
| 5,594,849 | A | 1/1997 | Kue et al. |
| 6,212,237 | B1 * | 4/2001 | Minami et al. ........... 375/240.16 |
| 6,326,786 | B1 | 12/2001 | Pruessmann et al. |
| 6,665,553 | B2 | 12/2003 | Kandori et al. |
| 7,169,111 | B2 | 1/2007 | Zhang et al. |
| 7,525,309 | B2 | 4/2009 | Sherman et al. |
| 7,742,806 | B2 | 6/2010 | Sternickel et al. |
| 2003/0018277 | A1 * | 1/2003 | He ................................ 600/544 |
| 2004/0260169 | A1 | 12/2004 | Sternnickel |
| 2005/0008255 | A1 * | 1/2005 | Aiso ............................ 382/284 |
| 2006/0119903 | A1 * | 6/2006 | Chiba et al. .................. 358/474 |
| 2006/0120580 | A1 | 6/2006 | Makram-Ebeid et al. |
| 2006/0122486 | A1 * | 6/2006 | Tamez-Pena et al. ......... 600/410 |
| 2007/0260151 | A1 | 11/2007 | Clifford |
| 2008/0278591 | A1 * | 11/2008 | Barna et al. ................. 348/216.1 |
| 2009/0060365 | A1 * | 3/2009 | Nagata et al. ................ 382/255 |
| 2009/0157331 | A1 | 6/2009 | Van Netten |
| 2009/0232213 | A1 * | 9/2009 | Jia ............................. 375/240.16 |
| 2010/0137727 | A1 * | 6/2010 | Sameni et al. ............... 600/511 |
| 2010/0280399 | A1 | 11/2010 | Francis et al. |
| 2011/0313274 | A1 * | 12/2011 | Subbarao ...................... 600/409 |

OTHER PUBLICATIONS

Agren, P.L., et al., "Magnetocardiographic Localization of Arrhythmia Substrates: A Methodology Study with Accessory Pathway Ablation as Reference", IEEE Trans. on Medical Imaging, vol. 17, No. 3, Jun. 1998.

(Continued)

Primary Examiner — Vani Gupta

(57) ABSTRACT

A magnetocardiogram (MCG) system with reduced noise artifacts is produced by first creating high-resolution image representations of low-resolution measurements obtained with a magnetic field sensor unit. The high-resolution image representations are created by use of a PCA model that has been trained using a library of ideal, no-noise, high-resolution images. The Biot-Sarvart Law is then used to create a 3D model of a current impulse, given the high-resolution image representations. From the 3D current impulse model, ideal sensor unit measurements as they would have been obtained using a theoretical sensor unit observing the 3D current impulse model are synthesized.

21 Claims, 24 Drawing Sheets

(56) References Cited

OTHER PUBLICATIONS

Jiang, S., et al., "ANN Interpolation in MCG Mapping", Proceedings of the 2005 IEEE, Engineering in Medicine and Biology, 27th Annual Conference Sep. 1-4, 2005.

Nomura, M., et al., "Evaluatiion of an Infarction Vector by Magnetocardiogram: Detection of Electromotive Forces that cannot be Deduced from an Electrocardiogram", International Congress Series 1300, pp. 512-515, 2007.

Stroink, G., "Forty Years of Magnetocardiology", BIOMAG2010, IFMBE Proceedings 28, pp. 1-8, 2010.

Tsukada, K., et al., "Newly Developed Magnetocardiographic System for Diagnosing Heart Disease", Hitachi Review, vol. 50, No. 1, pp. 13-17, 2001.

Weismuller, P., et al., "Magnetocardiographic Non-Invasive Localization of Accessory Pathways in the Wolff-Parkinson-White syndrome by a Multichannel System", European Heart Journal, 13, pp. 616-622, 1992.

Yamada, S., et al., "Noninvasive Diagnosis of Arrhythmic Foci by Using Magnetocardiograms Method and Accuracy of Magneto-Anatomical Mapping System", Journal of Arrhythmia, vol. 16, No. 5, pp. 580-586, 2000.

Yamada, S., et al., Magnetocardiograms in Clinical Medicine: Unique Information on Cardiac Ischemia, Arrhythmias, and Fetal Diagnosis, Internal Medicine, vol. 44, No. 1, Jan. 2005.

Fenici, R., et al., "Magnetocardiography provides non-invasive three-dimensional electroanatomical imaging of cardiac electrophysiology", Magnetocardiography and electroanatomical Imaging, Anatol J Cardiol 2007.

Erne, S. N., et al., "Magnetocardiography under Clinical Conditions", Biomedizinische Technik, vol. 44, No. s2, Jan. 1999.

Arturi, C. M., et al., "Information Content in Single-Component Versus Three-Component Cardiomagnetic Fields", IEEE Transactions on Magnetics, vol. 40, No. 2 Mar. 2004.

Jiang, S., et al., "Dipole Source Localization in Magnetocardiography", Proceedings of NFSI & ICFBI, Oct. 2007.

Fenici, R., et al., "Phantom Validation of Multichannel Magnetocardiography Source Localization", Pacing and Clinical Electrophysiology, vol. 26: pp. 426-430, 2003.

\* cited by examiner

FIG. 4

| SIMULATION | Random noise 0Setup 1 | | Random noise Setup 2 | | Random noise Setup 3 | |
|---|---|---|---|---|---|---|
| | Gaussian | Uniform | Gaussian | Uniform | Gaussian | Uniform |
| Real Measurement | 2.77 +/- 0.85 (%) | 3.71 +/- 0.83 (%) | 4.00 +/- 1.14 (%) | 5.13 +/- 1.15 (%) | 5.24 +/- 1.43 (%) | 6.65 +/- 1.37 (%) |
| High/Low-res Model Fitting (25 modes/25 modes) | 2.06 +/- 0.83 (%) | 2.44 +/- 0.77 (%) | 3.00 +/- 1.20 (%) | 3.48 +/- 1.13 (%) | 4.14 +/- 1.42 (%) | 4.63 +/- 1.36 (%) |
| | 2.14 +/- 1.45 (%) | 2.55 +/- 1.36 (%) | 3.07 +/- 2.60 (%) | 3.58 +/- 2.63 (%) | 4.24 +/- 4.10 (%) | 4.79 +/- 3.75 (%) |
| High-res Model Fitting + Dipole Reconstruction | 0.61 +/- 0.32 (%) | 0.78 +/- 0.31 (%) | 0.98 +/- 0.52 (%) | 1.17 +/- 0.48 (%) | 1.36 +/- 0.69 (%) | 1.49 +/- 0.62 (%) |

FIG. 5

| Simulation | Random noise Setup 4 | | Random noise Setup 5 | | Random noise Setup 6 | |
|---|---|---|---|---|---|---|
| | Gaussian | Uniform | Gaussian | Uniform | Gaussian | Uniform |
| Real Measurement | 6.05 +/- 1.47 (%) | 7.80 +/- 1.26 (%) | 10.30 +/- 2.27 (%) | 12.80 +/- 2.45 (%) | 16.60 +/- 4.67 (%) | 18.55 +/- 4.16 (%) |
| High/Low-res Model Fitting (25 modes/25 modes) | 3.67 +/- 1.46 (%) | 4.41 +/- 1.30 (%) | 7.08 +/- 2.31 (%) | 8.22 +/- 2.56 (%) | 12.76 +/- 4.57 (%) | 13.82 +/- 4.06 (%) |
| | 3.84 +/- 4.34 (%) | 4.61 +/- 3.16 (%) | 7.23 +/- 10.33 (%) | 8.36 +/- 11.98 (%) | 12.82 +/- 43.56 (%) | 14.11 +/- 34.65 (%) |
| High-res Model Fitting + Dipole Reconstruction | 1.69 +/- 0.99 (%) | 1.86 +/- 0.66 (%) | 3.65 +/- 4.02 (%) | 4.25 +/- 3.29 (%) | 11.45 +/- 10.83 (%) | 10.68 +/- 8.23 (%) |

| Phantom Exp | Z = 5cm | Z = 10cm | Z = 15cm |
|---|---|---|---|
| Real Measurement | 39.85 +/- 28.24 (%) | 38.22 +/- 28.61 (%) | 44.64 +/- 27.33 (%) |
| High/Low-res Model Fitting (20 modes/9 modes) | 32.36 +/- 25.18 (%) | 35.53 +/- 26.30 (%) | 45.93 +/- 24.44 (%) |
| | 31.43 +/- 24.05 (%) | 38.46 +/- 24.44 (%) | 44.28 +/- 24.44 (%) |
| High/Low-Res Model Fitting + Dipole Reconstruction | 26.02 +/- 20.00 (%) | 33.73 +/- 26.76 (%) | 39.54 +/- 20.80 (%) |
| | 26.24 +/- 20.76 (%) | 33.47 +/- 26.53 (%) | 38.94 +/- 20.74 (%) |

FIG. 6

$$\vec{B}(\vec{r_m}) = \frac{\mu_0}{4\pi} \frac{\vec{J}(\vec{p}) \times (\vec{r_m} - \vec{p})}{\|\vec{r_m} - \vec{p}\|^3}, m = 1 \cdots M \qquad Eq.\ 1$$

$$B_z(\vec{r_m}) = \frac{\mu_0}{4\pi} \frac{[-J^2, J^1] \cdot [r_m^1 - x_p, r_m^2 - y_p]'}{[(r_m^1 - x_p)^2 + (r_m^2 - y_p)^2 + (r_m^3 - z_p)^2]^{3/2}} \qquad Eq.\ 2$$

$$B_z(m) = \frac{a_m}{[b_m + (c-z)^2]^{3/2}} \qquad Eq.\ 3$$

$$B_z^m(z + \Delta z) = B_z^m(z) + \frac{d}{dz} B_z^m(z) \cdot \Delta z + \frac{d^2}{2dz} B_z^m(z) \cdot \Delta z^2 + O(\Delta z^3) \qquad Eq.\ 4$$

$$B_{xy}(i,j) = \sqrt{(\partial B_z(i,j)/\partial x)^2 + (\partial B_z(i,j)/\partial y)^2} \qquad Eq.\ 5$$

$$\vec{B^m} = \vec{J} \times \vec{R_m} = -\vec{R_m} \times \vec{J}$$

$$\text{where } \vec{B^m} = \vec{B}(\vec{r_m}),\ \vec{J} = \vec{J}(\vec{p}) \text{ and } \vec{R_m} = \frac{\mu_0}{4\pi} \frac{(\vec{r_m} - \vec{p})}{\|\vec{r_m} - \vec{p}\|^3} \qquad Eq.\ 6$$

FIG. 18A

$$\vec{B^m} = -[\vec{R_m}]_\times \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix} \quad Eq.\ 7$$

$$B_z^m = \begin{bmatrix} R_m^2, & -R_m^1 \end{bmatrix} \cdot \begin{bmatrix} J^1, J^2 \end{bmatrix}' \quad Eq.\ 8$$

$$\underbrace{\begin{bmatrix} B_z^1 \\ B_z^2 \\ \vdots \\ B_z^M \end{bmatrix}}_{\mathbf{B}} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{\mathbf{R}} \cdot \underbrace{\begin{bmatrix} J^1 \\ J^2 \end{bmatrix}}_{\mathbf{J}} \quad Eq.\ 9$$

$$\mathbf{J} = (\mathbf{R}^T \mathbf{R})^{-1} \mathbf{R}^T \mathbf{B} \quad Eq.\ 10$$

$$\vec{B^m} = \frac{\mu_0}{4\pi} \frac{\vec{J} \times ((\vec{r_0} + \vec{\delta_m}) - \vec{p})}{\|(\vec{r_0} + \vec{\delta_m}) - \vec{p}\|^3} = \frac{\mu_0}{4\pi} \frac{\vec{J} \times (\vec{\epsilon_0} + \vec{\delta_m})}{\|\vec{\epsilon_0} + \vec{\delta_m}\|^3} \quad Eq.\ 11$$

FIG. 18B

$$\alpha \vec{B}^m = \frac{\vec{J} \times \vec{\epsilon_0} + \vec{J} \times \vec{\delta_m}}{\|\vec{\epsilon_0} + \vec{\delta_m}\|^3} \qquad Eq.\ 12$$

$$\alpha B_z^m + \frac{-J^2 x_\epsilon + J^1 y_\epsilon + \tau_m^3}{((x_\epsilon + \delta_m^1)^2 + (y_\epsilon + \delta_m^2)^2 + (z_\epsilon + \delta_m^3)^2)^{3/2}} \\ = f^m(x_\epsilon, y_\epsilon, z_\epsilon) = 0 \qquad Eq.\ 13$$

$$z = d/\sqrt{2},\ \|\vec{J}\| = \frac{4\pi d^2 B_z^{max}}{0.385\mu_0} \qquad Eq.\ 14$$

FIG. 18C

Table 1. 2D Current Localization Error $\sqrt{(x_p - x_g)^2 + (y_p - y_g)^2}$

| Noise | 5% | 10% | 15% |
|---|---|---|---|
| Gaussian Distribution $G(0, 1)$ | 0.99 +/- 0.81 mm | 2.02 +/- 1.85 mm | 3.37 +/- 2.83 mm |
| Uniform Distribution $(0, 1)$ | 1.24 +/- 1.17 mm | 2.31 +/- 2.21 mm | 3.65 +/- 3.53 mm |

FIG. 19a

Table 2. 3D Current Localization Error $\sqrt{(x_p - x_g)^2 + (y_p - y_g)^2 + (z_p - z_g)^2}$

| Noise | 5% | 10% | 15% |
|---|---|---|---|
| Gaussian Distribution $G(0, 1)$ | 1.68 +/- 1.36 mm | 3.30 +/- 2.60 mm | 5.02 +/- 3.97 mm |
| Uniform Distribution $(0, 1)$ | 2.49 +/- 2.34 mm | 5.15 +/- 4.56 mm | 7.38 +/- 8.83 mm |

FIG. 19b

Table 3. Current Moment Reconstruction Error: Magnitude $\frac{\|\vec{J}_{rec}\| - \|\vec{J}_g\|}{\|\vec{J}_g\|}$

| Noise | 5% | 10% | 15% |
|---|---|---|---|
| Gaussian Distribution $G(0,1)$ | 2.2% +/- 1.8% | 4.7% +/- 4.6% | 6.0% +/- 5.7% |
| Uniform Distribution $(0,1)$ | 3.0% +/- 3.0% | 4.7% +/- 5.0% | 8.0% +/- 8.2% |

FIG. 19c

Table 4. Current Moment Reconstruction Error: Orientation $|atan2(x_p, y_p) - atan2(x_g, y_g)|$

| Noise | 5% | 10% | 15% |
|---|---|---|---|
| Gaussian Distribution $G(0,1)$ | 0.20° +/- 0.27° | 0.46° +/- 0.58° | 0.64° +/- 0.73° |
| Uniform Distribution $(0,1)$ | 0.30° +/- 0.32° | 0.77° +/- 0.95° | 1.02° +/- 1.12° |

FIG. 19d

```
# Sample number = K
# Dimension = 2Nx2N
# f₁ᵗ
# f₂ᵗ
  ⋮
# f_Kᵗ
```

First Implementation

$$A_{K\times(2N\times 2N)} = \begin{bmatrix} f_1^t \\ f_2^t \\ \vdots \\ f_K^t \end{bmatrix} \quad \text{(72)}$$

$$\tilde{A}_{K\times(2N\times 2N)} = \begin{bmatrix} f_1^t - f_{mean} \\ f_2^t - f_{mean} \\ \vdots \\ f_K^t - f_{mean} \end{bmatrix} = \begin{bmatrix} \tilde{f}_1^t \\ \tilde{f}_2^t \\ \vdots \\ \tilde{f}_K^t \end{bmatrix} \quad \text{(74)}$$

$$Cov_{K\times K} = \frac{1}{K}\tilde{A}\tilde{A}^t \quad \text{(76)}$$

Alternate Implementation

$$Cov = \frac{1}{K}\begin{bmatrix} \tilde{f}_1^t \\ \tilde{f}_2^t \\ \vdots \\ \tilde{f}_K^t \end{bmatrix}\begin{bmatrix} \tilde{f}_1 & \tilde{f}_2 & \cdots & \tilde{f}_K \end{bmatrix}$$

$$= \frac{1}{K}\begin{bmatrix} b_1^t \\ \vdots \\ b_L^t \end{bmatrix}\begin{bmatrix} b_1 & \cdots & b_L \end{bmatrix},\quad b_1 = \begin{bmatrix} \tilde{f}_1^t \\ \vdots \\ \tilde{f}_P^t \end{bmatrix}$$

$$= \frac{1}{K}\begin{bmatrix} b_1^t b_1 & \cdots & b_1^t b_L \\ \vdots & \cdots & \vdots \\ b_L^t b_1 & \cdots & b_L^t b_L \end{bmatrix}$$

8x8 sensors
17.5 x 17.5 cm

15x15 sensors
35 x 35 cm

Measurement Level I (mm)

| X<br>Y | 1 | 2 | 3 | 4 | 5 |
|---|---|---|---|---|---|
| 1 | 2.705 +/- 7.355 | 3.137 +/- 7.739 | 1.873 +/- 4.192 | 1.732 +/- 3.500 | 1.272 +/- 2.610 |
|   | 1.064 +/- 1.886 | 1.256 +/- 5.841 | 1.031 +/- 2.064 | 0.899 +/- 2.071 | 1.416 +/- 3.703 |
| 2 | 1.447 +/- 3.723 | 0.932 +/- 1.802 | 0.853 +/- 1.378 | 0.893 +/- 1.388 | 1.495 +/- 3.904 |
|   | 0.716 +/- 0.874 | 1.172 +/- 5.653 | 0.545 +/- 0.344 | 0.559 +/- 0.293 | 0.777 +/- 1.936 |
| 3 | 1.223 +/- 2.482 | 0.947 +/- 1.518 | 0.640 +/- 1.040 | 1.005 +/- 1.732 | 1.511 +/- 3.822 |
|   | 0.667 +/- 0.537 | 0.567 +/- 0.389 | 0.631 +/- 0.285 | 0.600 +/- 0.577 | 0.676 +/- 0.354 |
| 4 | 1.239 +/- 2.914 | 1.181 +/- 2.324 | 1.052 +/- 1.933 | 1.946 +/- 4.407 | 1.761 +/- 4.006 |
|   | 0.689 +/- 0.606 | 0.992 +/- 4.674 | 0.529 +/- 0.494 | 1.342 +/- 2.224 | 1.574 +/- 6.522 |
| 5 | 1.766 +/- 5.452 | 1.006 +/- 2.076 | 1.137 +/- 2.297 | 1.891 +/- 4.359 | 2.545 +/- 7.393 |
|   | 1.564 +/- 4.990 | 1.691 +/- 6.108 | 0.958 +/- 2.042 | 1.324 +/- 6.563 | 1.326 +/- 4.748 |

FIG. 26

Measurement Level II (mm)

| X<br>Y | 1 | 2 | 3 | 4 | 5 |
|---|---|---|---|---|---|
| 1 | 1.600 +/- 1.027 | 1.375 +/- 1.708 | 1.092 +/- 0.622 | 1.194 +/- 0.713 | 1.580 +/- 1.062 |
|   | 1.645 +/- 1.198 | 1.060 +/- 0.668 | 1.031 +/- 0.644 | 1.123 +/- 0.571 | 1.679 +/- 1.097 |
| 2 | 1.016 +/- 0.714 | 0.899 +/- 0.601 | 0.851 +/- 0.508 | 0.923 +/- 0.547 | 1.067 +/- 0.815 |
|   | 0.928 +/- 0.546 | 0.912 +/- 0.474 | 0.820 +/- 0.490 | 0.888 +/- 0.505 | 0.964 +/- 0.638 |
| 3 | 1.070 +/- 0.667 | 0.851 +/- 0.540 | 0.771 +/- 0.460 | 0.863 +/- 0.527 | 0.971 +/- 0.515 |
|   | 1.030 +/- 0.685 | 0.831 +/- 0.455 | 0.745 +/- 0.489 | 0.873 +/- 0.540 | 0.947 +/- 0.507 |
| 4 | 0.947 +/- 0.527 | 1.025 +/- 0.965 | 0.833 +/- 0.405 | 0.861 +/- 0.505 | 1.001 +/- 0.636 |
|   | 0.893 +/- 0.571 | 0.906 +/- 0.528 | 0.723 +/- 0.477 | 0.839 +/- 0.529 | 0.957 +/- 0.679 |
| 5 | 2.913 +/- 7.930 | 1.187 +/- 0.868 | 1.498 +/- 2.563 | 1.232 +/- 0.706 | 1.945 +/- 1.387 |
|   | 1.918 +/- 2.995 | 1.009 +/- 0.610 | 1.118 +/- 0.687 | 1.171 +/- 0.583 | 1.909 +/- 1.441 |

FIG. 27

Measurement Level III (mm)

| X \ Y | 1 | 2 | 3 | 4 | 5 |
|---|---|---|---|---|---|
| 1 | 3.511 +/- 8.966 | 2.224 +/- 1.365 | 1.770 +/- 1.227 | 2.134 +/- 2.500 | 2.639 +/- 2.041 |
|   | 2.762 +/- 2.046 | 2.166 +/- 1.413 | 1.860 +/- 1.332 | 2.040 +/- 1.238 | 2.601 +/- 1.923 |
| 2 | 1.949 +/- 1.422 | 1.425 +/- 0.965 | 1.420 +/- 0.895 | 1.609 +/- 1.172 | 1.823 +/- 2.026 |
|   | 1.825 +/- 1.123 | 1.407 +/- 0.930 | 1.239 +/- 0.799 | 1.461 +/- 0.861 | 1.656 +/- 0.899 |
| 3 | 1.585 +/- 1.073 | 1.394 +/- 0.978 | 1.158 +/- 0.629 | 1.265 +/- 0.730 | 1.631 +/- 1.099 |
|   | 1.447 +/- 0.897 | 1.253 +/- 0.781 | 1.144 +/- 0.759 | 1.255 +/- 0.810 | 1.329 +/- 0.826 |
| 4 | 2.076 +/- 1.320 | 1.554 +/- 1.043 | 1.474 +/- 0.932 | 1.522 +/- 1.091 | 1.867 +/- 1.238 |
|   | 1.870 +/- 1.143 | 1.386 +/- 0.856 | 1.409 +/- 0.847 | 1.521 +/- 1.038 | 1.784 +/- 1.272 |
| 5 | 2.537 +/- 1.541 | 2.015 +/- 1.271 | 1.759 +/- 1.141 | 1.924 +/- 1.282 | 2.858 +/- 1.915 |
|   | 3.048 +/- 5.839 | 1.770 +/- 1.103 | 1.737 +/- 1.197 | 1.813 +/- 1.458 | 2.911 +/- 3.525 |

FIG. 28

Measurement Level IV (mm)

| X \ Y | 1 | 2 | 3 | 4 | 5 |
|---|---|---|---|---|---|
| 1 | 4.320 +/- 3.837 | 3.443 +/- 1.893 | 3.123 +/- 1.984 | 3.137 +/- 1.878 | 4.422 +/- 3.122 |
|   | 4.047 +/- 2.433 | 3.318 +/- 2.408 | 2.950 +/- 1.892 | 3.006 +/- 1.989 | 3.601 +/- 2.378 |
| 2 | 2.919 +/- 2.009 | 2.501 +/- 1.745 | 1.983 +/- 1.276 | 2.429 +/- 1.473 | 2.834 +/- 1.712 |
|   | 2.870 +/- 2.182 | 2.426 +/- 1.616 | 2.100 +/- 1.404 | 2.207 +/- 1.460 | 2.627 +/- 1.544 |
| 3 | 2.402 +/- 1.709 | 1.923 +/- 1.211 | 1.844 +/- 1.290 | 1.735 +/- 1.117 | 2.876 +/- 3.334 |
|   | 2.246 +/- 1.298 | 1.859 +/- 1.104 | 1.825 +/- 1.268 | 1.934 +/- 1.137 | 2.597 +/- 1.596 |
| 4 | 2.747 +/- 1.802 | 2.358 +/- 1.456 | 1.850 +/- 1.527 | 2.445 +/- 1.713 | 2.894 +/- 2.044 |
|   | 2.512 +/- 1.487 | 2.147 +/- 1.299 | 2.135 +/- 1.215 | 2.402 +/- 1.497 | 2.791 +/- 1.964 |
| 5 | 4.477 +/- 6.871 | 3.106 +/- 2.114 | 2.972 +/- 1.987 | 3.511 +/- 5.339 | 5.805 +/- 7.400 |
|   | 4.286 +/- 2.975 | 3.199 +/- 2.101 | 2.786 +/- 1.689 | 3.410 +/- 2.137 | 5.214 +/- 5.535 |

FIG. 29

Measurement Level V (mm)

| X<br>Y | 1 | 2 | 3 | 4 | 5 |
|---|---|---|---|---|---|
| 1 | 6.902 +/- 5.579 | 5.159 +/- 3.290 | 5.914 +/- 11.284 | 5.784 +/- 11.699 | 5.871 +/- 4.336 |
|   | 5.752 +/- 3.845 | 4.999 +/- 3.152 | 4.043 +/- 2.758 | 4.963 +/- 3.425 | 5.746 +/- 3.854 |
| 2 | 4.498 +/- 3.042 | 3.497 +/- 2.537 | 3.436 +/- 2.091 | 3.539 +/- 2.106 | 3.966 +/- 2.357 |
|   | 4.304 +/- 3.022 | 3.730 +/- 2.465 | 3.212 +/- 2.205 | 3.343 +/- 2.291 | 3.747 +/- 2.199 |
| 3 | 4.292 +/- 8.690 | 3.165 +/- 1.883 | 3.134 +/- 2.095 | 3.305 +/- 2.398 | 3.478 +/- 2.293 |
|   | 3.801 +/- 2.370 | 3.192 +/- 2.152 | 2.777 +/- 1.880 | 2.906 +/- 1.794 | 3.313 +/- 1.868 |
| 4 | 4.523 +/- 3.204 | 3.287 +/- 2.035 | 3.847 +/- 8.668 | 4.656 +/- 7.973 | 4.158 +/- 2.935 |
|   | 4.031 +/- 2.359 | 3.271 +/- 2.326 | 3.451 +/- 2.288 | 3.672 +/- 2.700 | 4.246 +/- 3.015 |
| 5 | 5.821 +/- 7.453 | 5.294 +/- 5.726 | 6.604 +/- 12.962 | 6.282 +/- 7.363 | 6.965 +/- 5.558 |
|   | 5.567 +/- 4.883 | 4.985 +/- 4.946 | 4.429 +/- 3.238 | 5.364 +/- 4.242 | 6.347 +/- 4.858 |

FIG. 30

DENOISE MCG MEASUREMENTS

CROSS-REFERENCE TO RELATED APPLICATION(S)

This application is related to U.S. patent application Ser. No. 13/017,869 filed on Jan. 31, 2011 and entitled "High-Resolution Magnetocardiogram Restoration for Cardiac Electric Current Localization" the content of which is incorporated by reference herein in its entirety.

BACKGROUND

1. Field of Invention

The present invention relates the field of magnetocardiogram (MCG) imaging. More specifically, it relates to reducing the noise (i.e. de-noising) of sparse measurements obtained with an electromagnetic sensor unit.

2. Description of Related Art

The field of biomagnetism generally refers to the study of magnetic fields produced by living organisms, or living tissues. For example, this field has been applied to the creation of magnetic images of the human brain and heart. Of particular interest to the present invention is magnetocardiology, the creation of magnetic images of the human heart.

Cardiac electric currents (or current impulses) are generated by electrophysiological processes in the heart. Localizing abnormal electric currents may be used in diagnosing ischemic diseases such as myocardial infarction, angina cordis, etc. It also benefits patients in the catheter lab for both treatment and follow-up, as is explained in "Forty Years of Magnetocardiology", by F. Stroink, in Int. Conf. on Biomagnetism Advances in Biomagnetism, 28:1-8, 2010.

Traditionally, irregular cardiac electric activity, such as arrhythmia, is diagnosed by means of an electrocardiogram (ECG). However, an ECG only provides temporal information, and thus cannot localize abnormal electric impulse currents in the heart directly, even if the ischemic disease has been detected. One technique to attempt to localize electrical impulse currents is known as Body Surface Potential Mapping (BSPM), which uses a large number of electrodes (i.e., leads) to reconstruct a body surface potential map. This BSPM technique is explained in "Noninvasive volumetric imaging of cardiac electrophysiology", by Wang et al., in *CVPR*, pages 2176-2183, 2009. The accuracy of BSPM electric current localization, however, is limited because the observed electrical signals can be distorted by the poor conductivity of body tissue.

The advent of the magnetocardiogram, or magnetocardiography, (MCG) made available more accurate measurements of cardiac electric impulse currents, both spatially and temporally. With reference to FIG. 1A, an MCG system consists of an MCG sensor unit 11 housing a small number of individual electromagnetic sensors 13 (typically arranged as a planar array of sixty-four or fewer sensors). Electrical impulses 17 within the body create a magnetic field 15. In the present case, the human heart 19 functions as the observed source of electrical impulses 17 (i.e. as the current source).

Each electromagnetic sensor 13 is a capture point, and hereinafter may be referenced as a capture 13. Each capture 13 measures a one-dimensional (i.e. 1D) magnetic waveform in a direction perpendicular to the sensor planar array (i.e. the z-direction) emanating from the patient's chest 21 (i.e. human torso). By aligning (or synchronizing) the depth measures (i.e. the 1D magnetic waveform) of the array of captures 13 at a given depth in the z-direction, a two-dimensional (2D) MCG map at the given depth may be constructed. The MCG sensor unit 11 is usually placed five to ten centimeters above the patient's chest 21, and measures the patient's heart magnetic field in a non-invasive manner. Thus, the array of captures 13 measure a collection of low resolution (hereinafter, low-res), two-dimensional (2D) MCG maps of electromagnetic activity.

MCG has a few advantages over ECG. First, the magnetic field generated by the heart's electrical current impulses (hereinafter, currents, electric currents or electrical currents) is not distorted in the direction perpendicular to the body surface (i.e., z direction), due to the magnetic property of body tissue. Thus MCG is more accurate and sensitive to weak electrical activity in the early stage of heart disorders. Second, the MCG sensor array can localize the position of electrical currents in the heart. Finally, MCG measurements are non-invasive. After forty years of research in MCG, cardiac electric current localization and high resolution visualization for MCG measurements are attracting more and more interest from both research and clinical areas.

However, there are a number of difficulties associated with MCG, which so far has prevented MCG from becoming a mainstream medical diagnostic tool in cardiology. A first difficulty is the great amount of electromagnetic noise that can obscure the small magnetic fields created in a human heart. This has been addressed, to some extent, by using a magnetically-shielded room to reduce background noise and by the introduction of a sensitive electromagnetic sensor 13, such as the superconducting quantum interference device (SQUID). Although these steps have helped, the raw readings nonetheless remain more noisy than desired.

Another difficulty is the limited number of electromagnetic sensors 13 that that may be housed within an MCG sensor unit 11, which limits the resolution of an MCG map. As a result, the MCG sensor unit 11 can typically produce only low resolution (low-res) 2D MCG maps. Typically, these low-res 2D MCG maps are not sufficient for localizing electric currents in the heart. For example, a 64 channel Hitachi™ MCG system with a 25 mm sensor interval (as described in "Newly Developed Magnetocardiographic System for Diagnosing Heart Disease", by Tsukada et al., in *Hitachi Review*, 50(1): 13-17, 2001) only measures an 8×8 MCG map (i.e. an 8×8 array of 64 measurement points).

Thus, a necessary step in MCG is generating a high resolution (hereinafter high-res) 2D MCG image, or map, from a low-res 2D MCG image, or map. Two image examples 23 and 25 of such high-res 2D MCG images are shown in FIG. 1B. Image 23 shows the tangential image of a generated high-res MCG image of a healthy heart. The maximal point (i.e. strongest point) within image 23 indicates the location (or source) of electric current in the heart. Thus, high-res MCG images permits doctors to directly "see" the electrical activity in the heart. Image 25 shows the tangential image of a generated high-res MCG image of an unhealthy heart. It differs significantly from image 23 of a healthy heart, and thus provides important cues for diagnosis. Compared to low-res MCG maps, high-res MCG images provide more diagnostic significance, and serve as the basis for an accurate electric current localization.

Most modern MCG systems use curve fitting interpolation methods between observed measurements of the electromagnetic sensors 13 to construct high-res 2D MCG images from the low-res 2D MCG maps, such as shown in "Magnetocardiographic Localization of Arrhythmia Substrates: A Methodology Study With Accessory Path-Way Ablation as Reference", by B. A. S. et al., in *Ann Noninvasive Electrocardiol*, 10(2):152-160, 2005, and shown in "Evaluation of an Infarction Vector by Magnetocardiogram: Detection of Electromotive Forces that Cannot be Deduced from an Electrocardiogram", by Nomura et al, in *Int. Congress Series*, 1300:512-515, 2007. Unfortunately, the accuracy of curve fitting methods is typically limited.

What is needed is an MCG system that successfully further reduces the noise in observed low-res MCG maps.

Also needed is a method of better utilizing the high-res MCG maps to improve the observed measurements of an MCG system.

SUMMARY OF INVENTION

An object of the present invention an MCG system with improved de-noising capabilities.

Another object of the present invention is to utilize the improved resolution of a high-res MCG image to help correct for noise in an observed low-res MCG map.

A further object of the present invention is to provide a method of generating a high-res MCG image having inherent noise-reducing capabilities.

Another object of the present invention is to produce high-res MCG images that provide imaging information beyond the boundaries of the MCG sensor unit.

A further object of the present invention is to provide an approach toward generating high-res MCG images from low-res 2D maps that reduce the computing resource requirements of an MCG system.

The above objects are met in a magnetocardiogram (MCG) system having: a sensor unit including M×M electromagnetic sensors producing a sparse measurement output of M×M data values, the sparse measurement output constituting a first MCG image; a high resolution MCG image synthesizer for receiving the first MCG image and producing a higher resolution image representation of the first MCG image, the higher resolution image representation being a second MCG image of higher pixel density than the first MCG image; and a de-noising image processing block for receiving the second MCG image and producing a de-noised lower resolution image representation of the second MCG image, the de-noised lower resolution image representation being a third MCG image having M×M picture elements within a physical sensor area corresponding to the span of the M×M data values of the first MCG image and having a reduced noise level as compared to the first MCG image.

Preferably, the de-noising image processing block identifies as target picture elements the picture elements of the second MCG image whose image locations correspond to the image locations of the M×M data values of the first MCG image, and populates the physical sensor area with the target pictures elements.

Additionally the producing of the second MCG image by the high resolution MCG image synthesizer includes: accessing a linear model defining a model MCG image of higher resolution than the first MCG image, the linear model establishing interpolation patterns between characteristics of the linear model and any data value of the sparse measurement output of M×M data values; and producing an intermediate MCG image by projecting the first MCG image onto the subspace of the linear model, and establishing coefficients for the intermediate MCG image in accordance with the linear model and the M×M data values. In this case, the high resolution MCG image synthesizer outputs the intermediate image as the second MCG image.

Also in this case, the linear model is defined by creating a plurality of synthesized magnetocardiogram images having the same resolution as the second MCG image, the synthesized magnetocardiogram images being based on simulated electrical impulses within a three-dimensional spatial heart volume, as it would be perceived in an expected magnetocardiogram system. Preferably, the synthesized MCG images are based on randomly generated currents within the heart volume, and the linear model is created by using principal component analysis (PCA).

Preferably in this embodiment, the interpolation patterns are established by the following steps: (A) defining the following notation: N×N dense Bz magnetic field map to form a vector; M×M sparse measurement to form a vector; K randomly generated single current dipoles Q; (B) for each randomly generated current Q, computing an N×N magnetic field map using Biot-Savart equation and stack the resultant image to a vector $f_1$; (C) repeating step (B) to obtain K samples and getting a data matrix $A=[f_1, f_2, \ldots f_K]$; and (D) training a PCA model given input data A, to obtain the eigenmatrix $\Sigma_f$.

Also in this embodiment, the intermediate MCG image is created by: given a new dipole and M×M sparse measurements $g_j$, finding the corresponding rows in the eigenmatrix, and denoting a resultant submatrix as $\Sigma_g$; projecting the sparse measurement to the PCA subspace and computing the coefficients as $c_g=\Sigma_g^+(g_j-g_{mean})$, where $\Sigma_g^+$ is the pseudo inverse of $\Sigma_g$; and using the computed coefficients and original PCA space to reconstruct the dense magnetic field map Bz, as $f_j=\Sigma_f c_g+f_{mean}$.

Further preferably, the producing of the intermediate MCG image may include: defining the sparse measurement output as a vector g; defining the linear model as $\Sigma$; extracting from $\Sigma$ the row corresponding to sparse measurement output to form a sub-eigenmatrix $\Sigma_g$; projecting g onto $\Sigma_g$; defining the establishment of coefficients as $c_g=\Sigma_g^+(g_t-\mu_g)$, where $\Sigma_g^+$ is the pseudo inverse of $\Sigma_g$, $\mu_g$ are extracted coefficients from a mean vector $\mu$ of linear model $\Sigma$; and defining the intermediate MCG image vector h as $h=\Sigma_f c_g+\mu$.

Optionally, the high resolution MCG image synthesizer includes an electric current localizer for determining a position and momentum of an electric current in accord with the intermediate MCG image, the electric current localizer evaluating the electromagnetic output data from each electromagnetic sensor in an x-y orientation (Bxy) assuming single dipole, computing dense Bxy from dense Bz, finding the image maximum in the intermediate MCG image, and using this determined position information as a starting point in an iterative process for identifying a three-dimensional position vector $\vec{p}$ and momentum vector $\vec{J}$ for the electric current; and the high resolution MCG image synthesizer uses the Biot-Sarvart Law for producing the second MCG image based on the identified three-dimensional position vector $\vec{p}$ and momentum vector $\vec{J}$.

Additionally, the identifying of the three-dimensional position vector $\vec{p}$ and momentum vector $\vec{J}$ for the electric current may further include: given the third MCG image $B_z(i,j)(i=1, 2, \ldots, N; j=1, 2, \ldots, N)$, the maximal point of the tangential components $B'_{xy}(i,j)$ of $B_z(i,j)$ refers to the 2D position $(x_p, y_p)$ of the electric current, and the tangential components of $B_z(i,j)$ is computed as $B_{xy}(i,j)=\sqrt{(\partial B_z(i,j)/\partial x)^2+(\partial B_z(i,j)/\partial y)^2}$; and the iterative process for identifying position vector $\vec{p}$ and momentum vector $\vec{J}$ for the electric current includes: (a) defining the Biot-Sarvart Law as $\vec{B}^m=\vec{J}\times\vec{R}_m=-\vec{R}_m\times\vec{J}$, where $\vec{B}^m=\vec{B}(\vec{r}_m)$, $\vec{J}=\vec{J}(\vec{p})$ and $$\vec{R}_m = \frac{\mu_0}{4\pi} \frac{(\vec{r}_m - \vec{p})}{|\vec{r}_m - \vec{p}|^3};$$

(b) expanding this definition of the Biot-Sarvart Law to a matrix form by using a skew-symmetric matrix:

$$\vec{B}^m = -[\vec{R}_m]_x \vec{J}$$

$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix}$$

where the z component of the magnetic field is computed as:

$$B_z^m = [R_m^2, -R_m^1] \cdot [J^1, J^2]'$$

where $R_m^1$, $R_m^2$ are x,y components of $\vec{R}_m$, and for the M×M electromagnetic sensors one has a linear system:

$$\underbrace{\begin{bmatrix} B_z^1 \\ B_z^2 \\ \vdots \\ B_z^M \end{bmatrix}}_{B} = \underbrace{\begin{bmatrix} R_1^2 & -R_1^1 \\ R_2^2 & -R_2^1 \\ \vdots & \vdots \\ R_M^2 & -R_M^1 \end{bmatrix}}_{R} \cdot \underbrace{\begin{bmatrix} J^1 \\ J^2 \end{bmatrix}}_{J}$$

where B is a measured M×1 vector, R is a M×2 position matrix that is computed from given $\vec{p}$ and $\vec{\delta}_m$, and a lease squares solution for J provides an estimation of J defined as $J = (R^T R)^{-1} R^T B$; (c) defining the Biot-Sarvart Law as $$\vec{B}^m = \frac{\mu_o}{4\pi} \frac{\vec{J} \times ((\vec{r}_o + \vec{\delta}_m) - \vec{p})}{\|(\vec{r}_o + \vec{\delta}_m) - \vec{p}\|^3}$$

$$= \frac{\mu_o}{4\pi} \frac{\vec{J} \times (\vec{\varepsilon}_o + \vec{\delta}_m)}{\|(\vec{\varepsilon}_o + \vec{\delta}_m)\|^3}$$

letting $\alpha = 4\pi/\mu_0$ and $\vec{\varepsilon}_0 = \vec{r}_0 - \vec{p}$, identifying $\vec{\delta}_m$ as known for each sensor to redefining the Biot-Sarvart Law as $$\alpha \vec{B}^m = \frac{\vec{J} \times \vec{\varepsilon}_o + \vec{J} \times \vec{\delta}_m}{\|(\vec{\varepsilon}_o + \vec{\delta}_m)\|^3}$$

letting $\vec{\tau}_m = \vec{J} \times \vec{\delta}_m$ and $\vec{\varepsilon}_0 = (x_\epsilon, y_\epsilon, z_\epsilon)^T$ and computing $\vec{\tau}_m$ from $\vec{J}$, for each sensor m=1: M, defining a nonlinear equation in terms of $(x_\epsilon, y_\epsilon, z_\epsilon)$ as $$\alpha \vec{B}^m + \frac{-J^2 x_\varepsilon + J^1 y_\varepsilon + \tau_m^3}{((x_\varepsilon + \delta_m^1)^2 + (y_\varepsilon + \delta_m^2)^2 + (z_\varepsilon + \delta_m^3)^2)^{3/2}} = f^m(x_\varepsilon, y_\varepsilon, z_\varepsilon) = 0$$

letting $F = (f^1; f^2; \ldots; f^M) = 0$, and solving a least squares solution of the nonlinear system F for $\vec{\epsilon}_0$; (d) using $\vec{\epsilon}_0$ from step (c) to update the position matrix R and recompute J as in step (b), and iteratively repeating steps (b) and (c) until converges is achieved; and (e) defining the $\vec{p} = \vec{r}_0 - \vec{\epsilon}_0$, and defining the initial depth z and magnitude $\|\vec{J}\|$ the electric current as $$z = d/\sqrt{2.3} \text{ cm},$$

$$\|\vec{J}\| = \frac{4\pi d^2 B_z^{max}}{0.385 \mu_0}$$

where d is the distance between two magnetic poles in the third MCG image.

Preferably, the second MCG image spans an imaging area greater than the first MCG image. In this case, the third MCG image spans an imaging area greater than the first MCG image; the pixel density of the third MCG image's physical sensor area is uniformly extended throughout the third MCG image; and the pixels of the third MCG image that lay beyond the physical sensor area are populated with simulated sensor data determined from the second MCG image.

Additionally, the de-noising image processing block identifies as target pixels the picture elements of the second MCG image whose pixel image locations correspond to the pixel image locations of the third MCG image, and populates the pixel image locations of the third MCG with their corresponding target pictures elements.

Preferably, the imaging span of the third MCG image is substantially the same as the imaging span of the second MCG image.

Optionally, the producing of the higher resolution image representation of the first MCG image by the high resolution MCG image synthesizer includes: accessing a linear model defining a model MCG image of substantially higher resolution than the first MCG image, the linear model being defined by creating a plurality of synthesized magnetocardiogram images having the same size and resolution as the second MCG image; the synthesized magnetocardiogram images being based on simulated electrical impulses within a three-dimensional spatial heart volume, as it would be perceived in a hypothetical magnetocardiogram system of similar resolution as the second MCG image; information from the plurality of synthesized magnetocardiogram images being incorporated into the linear model to establish interpolation patterns between characteristics of the linear model and any data value of the sparse measurement output; and the producing of the second MCG image including the projecting the first MCG image onto the subspace of the linear model to establishing coefficients for use in the creation of the second MCG image.

In the case, the linear model is defined by: (A) defining K simulated electrical impulse current dipoles Q; (B) for each simulated electrical impulse Q, computing an N×N magnetic field map using Biot-Savart equation and stacking the resultant image to a vector $f_1$, so as to define a data matrix $A = \lfloor f_1, f_2, \ldots f_K \rfloor$ for the K simulated electrical impulses; (C) defining a mean vector from the data matrix A of vectors; and (D) defining a covariance matrix by determining the vector components needed for constructing the covariance matrix from the data matrix A, dividing the covariance matrix into L×L blocks, computing each of the L×L blocks separately by accessing into an active data memory only the vector components needed the L×L block being currently processed, storing the computed result for L×L block being currently processed, and combining the results of all L×L blocks.

The objects are also met in a magnetocardiogram (MCG) system having: a sensor unit including M×M electromagnetic sensors producing a sparse measurement output of M×M data values, the sparse measurement output constituting a first MCG image; a high resolution MCG image synthesizer for receiving the first MCG image and producing a higher resolution image representation of the first MCG image, the higher resolution image representation being a second MCG image of higher pixel density than the first MCG image and spanning an imaging area greater than the first MCG image.

Preferably, the producing of the higher resolution image representation of the first MCG image by the high resolution MCG image synthesizer includes: accessing a linear model defining a model MCG image of substantially higher resolution than the first MCG image, the linear model being defined by creating a plurality of synthesized magnetocardiogram images having a substantially similar size and resolution as the second MCG image; the synthesized magnetocardiogram images being based on simulated electrical impulses within a three-dimensional spatial volume as it would be perceived in a hypothetical magnetocardiogram system of similar resolution and image size as the second MCG image; information from the plurality of synthesized magnetocardiogram images being incorporated into the linear model to establish interpolation patterns between characteristics of the linear model and any data value of the sparse measurement output; and the producing of the second MCG image including the projecting the first MCG image onto the subspace of the linear model to establishing coefficients for the second MCG image.

Optionally, the three-dimensional spatial volume is a simulated heart tissue volume; the synthesized MCG images are based on randomly generated currents within the simulated heart tissue volume; and the linear model is created by using principal component analysis (PCA).

Preferably, the linear model is defined by: (A) defining K simulated electrical impulse current dipoles Q; (B) for each simulated electrical impulse Q, computing an N×N magnetic field map using Biot-Savart equation and stacking the resultant image to a vector $f_1$, so as to define a data matrix $A=[f_1, f_2, \ldots f_K]$ for the K simulated electrical impulses; (C) defining a mean vector from the data matrix A of vectors; and (D) defining a covariance matrix by determining the vector components needed for constructing the covariance matrix from the data matrix A, dividing the covariance matrix into L×L blocks, computing each of the L×L blocks separately by accessing into an active data memory only the vector components needed the L×L block being currently processed, storing the computed result for L×L block being currently processed, and combining the results of all L×L blocks.

Other objects and attainments together with a fuller understanding of the invention will become apparent and appreciated by referring to the following description and claims taken in conjunction with the accompanying drawings.

BRIEF DESCRIPTION OF THE DRAWINGS

In the drawings wherein like reference symbols refer to like parts.

FIGS. 4 to 6 show some de-noise results obtained by the present invention.

FIGS. 18a to 18c show various equations useful in explanation of the present invention.

FIGS. 19a to 19d show various tables showing test results.

FIG. 22 compares some aspects of the implementation of the original model and the expanded model.

FIGS. 26 through 30 provide tables comparing experimental results comparing the original model to the expanded model according to the levels illustrated in FIG. 24.

DESCRIPTION OF THE PREFERRED EMBODIMENTS

Figure 1A:
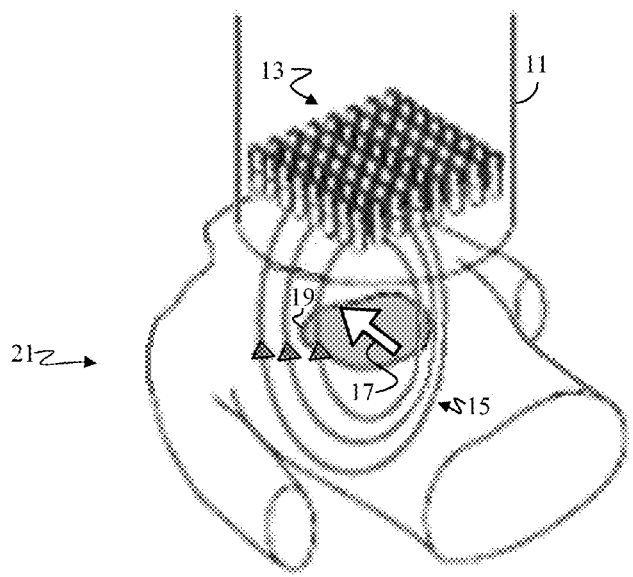
FIG. 1a illustrates an MCG measurement system in accord with the present invention.

Magnetic fields generated by a human heart are very weak. Typically, such magnetic fields are in the order of $10^{-12}$ to $10^{-10}$ Tesla. The size of these field means that they are inherently vulnerable to electromagnetic noise. Obtaining good measurements therefore means using highly sensitive equipment, but such sensitivity are likewise susceptible to noise.

Therefore, even the best MCG measurements are liable to be noisy. In fact, raw MCG measurements may be too noisy for direct use. Consequently, de-noise methods (i.e. methods for removing noise from a raw MCG map) are typically part of required pre-processing step in the generation of a 2D MCG image.

Different approaches address different types of noise. For example, environmental noise may be reduced by use of a shielded room and gradiometer. System noise may be reduced by careful calibration of equipment. Direct measurement noise in raw data is typically addressed by signal processing methods.

Current signal processing methods typically address measurement noise only in one-dimension. That is, observed data signals from each individual electromagnetic sensor are processed separately. Since the observed measurements from each electromagnetic sensor are gathered over time, such signal processing methods provide de-noising of only one-dimensional information in the temporal domain.

The presently preferred invention focuses on reducing direct measurement noise, but does so by applying a two-dimensional de-noise method. That is, instead of processing each electromagnetic sensor individually over time as in the prior art, in the present invention, an entire array of electromagnetic sensors within an MCG sensor unit is addressed simultaneously within the spatial domain. Thus, the present invention provides a de-noise method for two-dimensional measurements over a given imaging area.

The present de-noise methods takes the approach that measurement noise for each electromagnetic sensor can be considered as an addictive random noise with zero mean. That is, a noisy measurement $\hat{z}$ is the sum of a clean measurement z plus random noise in three dimensions σ(x, y, t), as follows:

$$\hat{z}(x,y,t) = z(x,y,t) + \sigma(x,y,t)$$

Using this approach, noise can be removed by solving a least square problem. More pertinent to the presently preferred approach, the noise may be removed by fitting a PCA model since the noise will not be the dominant mode.

By using a PCA model one may simultaneously apply additional image processing enhancements during the de-noise processing. That is, the PCA model may be designed for additional image processing effects, which become an integral part of the de-noise process. Thus, the PCA model may adjust (i.e. modify or filter) the input raw MCG map while removing noise.

Thus, the presently preferred embodiment provides a method of applying image enhancement(s) to the low-res, 2D MCG image while in the process of removing noise. This image enhancement(s), for example, may be in the form of providing improved modeling of observed magnetic fields and/or in the form of increasing the scope (i.e. the viewable area) of the original low-res MCG image.

In one approach, the method constructs a three-dimensional (3D) current vector representative of the raw low-res, 2D MCG map, and then reconstructs an ideal, low-res, 2D MCG map from the constructed 3D current vector as it would have been captured by a theoretical, noiseless MCG unit. Preferably, the steps for constructing the 3D current vector incorporate a PCA model that enhances the accuracy of the constructed 3D current vector while simultaneously suppressing measurement noise. In another approach, the PCA model is applied without the subsequent 3D current vector construction. A de-noised low-res, 2D MCG map as it would be seen by a noiseless MCG unit is constructed directly from the PCA model results.

In both cases, the PCA model may be augmented to provide a larger viewing area than that provided by the original physical MCG unit. Consequently, the resultant low-res, 2D MCG map constructed from the enhanced PCA model provides a larger viewing area than that of the original raw, low-res, 2D MCG map. This reduces some of the errors prone to boundary edge conditions, such as the edges of the array of physical electromagnetic sensors.

Figure 1B:
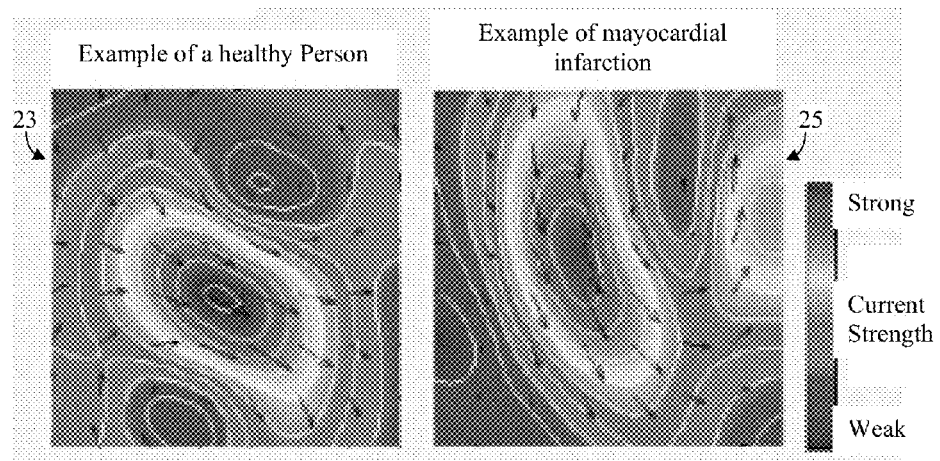
FIG. 1b compares the tangential image of a restored high-res MCG image of a healthy heart with that of an unhealthy heart.
Figure 2:
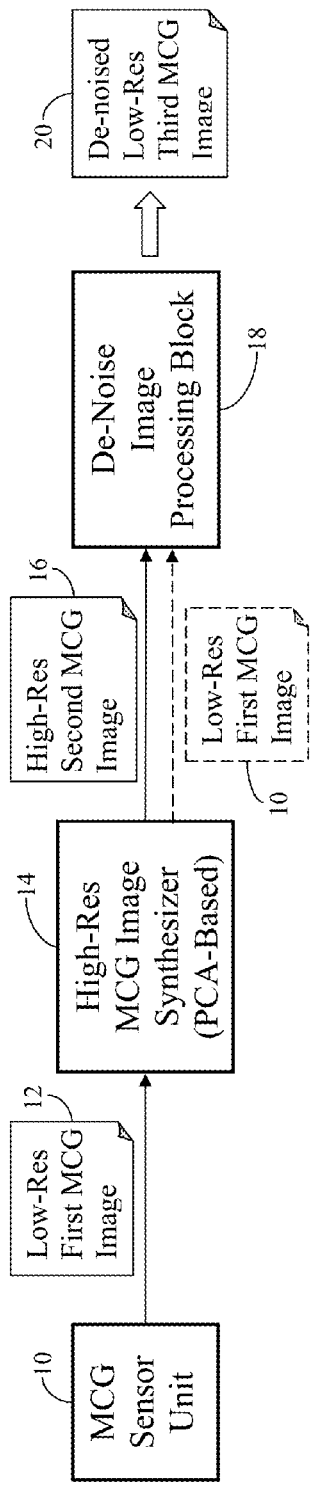
FIG. 2 is a general overview of the present de-noise method/system.

With reference to FIG. 2, a general overview of the present invention begins with a physical MCG sensor unit 10 (such as sensor unit 11 of FIG. 1) that outputs a low-res, 2D first MCG image 12 (or sparse MCG map). As it would be understood, MCG sensor unit 10 would house an array of physical electromagnetic sensors, as illustrated in FIG. 1, and each electromagnetic sensor would provide a separate measurement output, or data value, which constitutes a pixel value. For example, if MCG sensor unit 11 houses an array M×M electromagnetic sensors, low-res first MCG image 12 would have an M×M pixel resolution comprised of the M×M data values.

Low-res first MCG image 12 is sent to a (preferably PCA-based) high-res MCG image synthesizer 14 that produces a high-res, 2D second MCG image 16. High-res second MCG image 16 is a higher resolution image representation of first MCG image 12. For example, second MCG image 16 may have a P×P pixel resolution, where P>>M. Further preferably, second MCG image 16 has a consistent, higher pixel density than first MCG image 12. For example, if first MCG image 12 spans an image area of 20 cm×20 cm, then its pixel density would be M×M pixels per 400 cm$^2$, whereas the pixel density for the corresponding, same image area of second MCG image 16 would be P×P pixels per 400 cm$^2$. It is noted that if the image area of second MCG image 16 is bigger than that of first MCG image 12, then second MCG image 16 preferably maintains the same pixel density over its entire image area.

A De-noise image processing block 18 receives high-res second MCG image 16. De-noise image processing block 18 is preferably aware of at least the physical construct and arrangement of MCG sensor unit 10 and its internal array of electromagnetic sensors. De-noise image processing block 18 uses this information to construct, from second MCG image 16, a low-res 2D third MCG image 20 that simulates what MCG Sensor unit 10 should have captured if measurement noise were absent from its readings. That is, de-noise image processing block 18 simulates the physical sensor area of MCG sensor unit 10, i.e. the imaging area of first MCG image 12. Therefore, third MCG image 20 has a similar (preferably equal) pixel density as first MCG image 12.

Optionally, de-noise image processing block 18 may also achieve this by receiving a copy of first MCG image 12, as illustrated by dotted lines. In this case, de-noise image processing block 18 may compare first MCG image 12 to second MCG image 16, and identify as target picture elements the picture elements of second MCG image 16 whose image locations correspond to the image locations of the M×M data values of first MCG image 12. The image area of third MCG image 20 that correspond to the image area of first MCG image 12 (i.e. that correspond to the physical sensor area of MCG sensor unit 10) may then be populated with the corresponding target pictures elements.

It is desirable that the image area of third MCG image 20 be similar to (and preferably the same as) the image area of second MCG image 16, and that the pixel density of third MCG image 20 be similar to (and preferably the same as) first MCG image 12. Thus, if second MCG image 16 is larger than, and fully encompasses, the image area of first MCG image 12, then the third MCG image 20 would likewise be larger than, and fully encompass, the image area of first MCG image 12. In this case, the pixel density of the third MCG image's sensor area (i.e. the image area that corresponds to the image area of first MCG image 12) is uniformly extended throughout third MCG image 20. Preferably within third MCG image 20, the pixels that lay beyond this sensor area are populated with simulated sensor data determined from second MCG image 16 in a manner similar to that descried immediately above, and/or described in more detail below.

As is explained above, high-res MCG image synthesizer 14 preferably implements a PCA-based model, and provides image enhancement while at the same time increasing the resolution and reducing the nose of first MCG image 12. A simplified internal view of MCG image synthesizer 14 is provided in FIG. 3.

Figure 3:
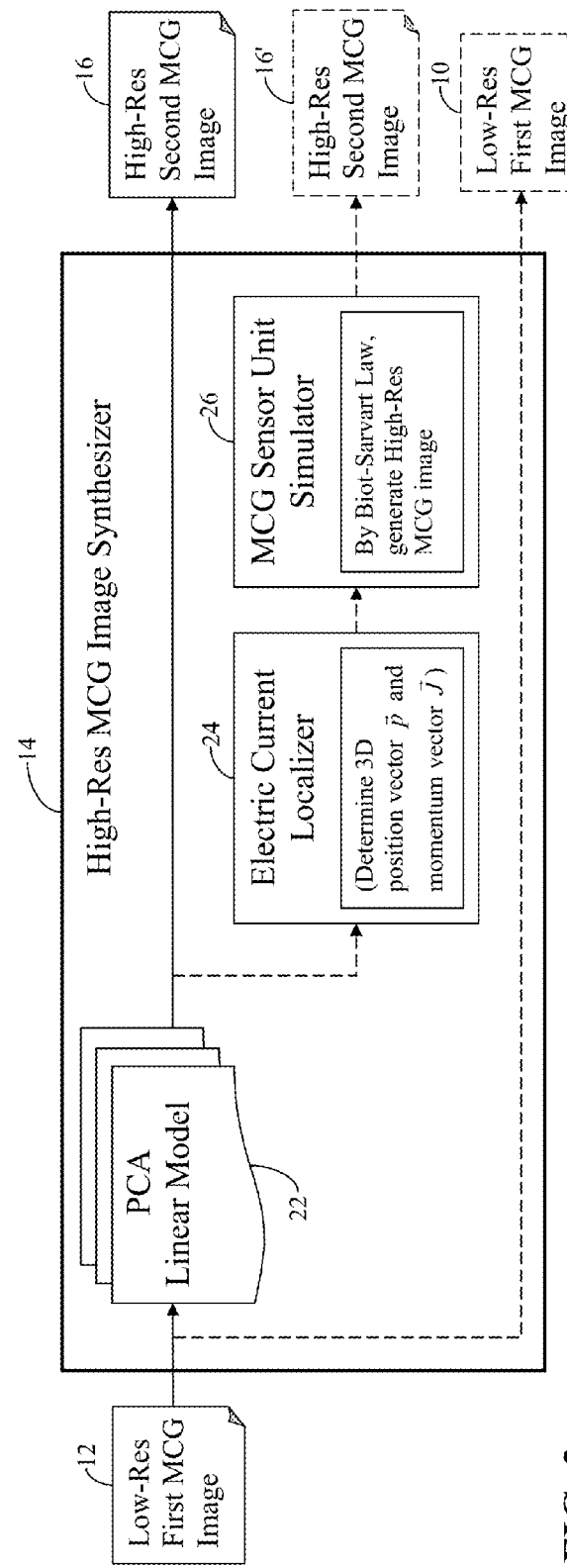
FIG. 3 shows a simplified internal view of the MCG image synthesizer of FIG. 2.

With reference to FIG. 3, where all elements similar to FIG. 2 have similar reference characters and are described above, a few optional implementations of MCG image synthesizer 14 are shown. As illustrated in FIGS. 2 and 3, MCG image synthesizer 14 may pass input first MCG image 12 directly to an output for transferring to de-noise image processing block 18.

Preferably, MCG image synthesizer 14 incorporates, or is in communication with, a model MCG image (herein embodied by PCA linear model 22) of substantially higher resolution than said first MCG image 12. PCA Linear Model 22 modifies first MCG image 12 based on prior knowledge of ideal high resolution images having desired effects of current impulses in heart tissue. Since it is impractical to obtain a library of such ideal high resolution image from physical measurement, PCA linear model 22 is preferably defined from a library of synthesized magnetocardiogram images having the same size and resolution as second MCG image 16. The library of synthesized magnetocardiogram images is preferably synthesized to incorporate desired image enhancements. Consequently PCA linear model 22, which is based on this synthesized library, will incorporated the same desired image enhancements. As is explained more fully below, the synthesized magnetocardiogram images are based on simulated random electrical impulses within a three-dimensional spatial heart tissue volume, as they would be perceived in a hypothetical high resolution magnetocardiogram system. Information from this plurality of synthesized magnetocardiogram images are incorporated into PCA linear model 22 to establish interpolation patterns between characteristics of the linear model and any data value of first MCG image 12. A first technique for producing second MCG image 16 is to project first MCG image 12 onto the subspace of PCA linear model 22 to establishing coefficients for use in the creation of second MCG image 16.

In one embodiment, the resultant high resolution image output by PCA Linear model 22 is sent directly to an output as second MCG image 16.

In an alternate embodiment, MCG image synthesizer 14 further models a 3D current impulse from the high-res image produced by PCA liner model 22, and then recreates a second MCG image 16' from the modeled 3D current impulse. This further reduces the noise of the final high-res image, as is explained more fully below.

In this alternate case, the output from PCA liner model 22 is an intermediate image that is passed to an electric current localizer 24, which determining a position and momentum of an electric current in accord with the intermediate MCG image. Preferably, electric current localizer 24 evaluates electromagnetic output data as they would be observed in individual electromagnetic sensors in an x-y orientation (Bxy) assuming a single dipole and computes a dense Bxy from a dense Bz, where "B" refers to a magnetic field. Electric current localizer 24 then finds the image maximum in the intermediate MCG image, and uses this determined position information as a starting point in an iterative process for identifying a three-dimensional position vector $\vec{p}$ and momentum vector $\vec{J}$ for the electric current.

The resultant 3D position vector $\vec{p}$ and momentum vector $\vec{J}$ is then passed to an MCG sensor unit simulator 26, which generates second MCG image 16' based on simulation models of how an electric field generated by a current impulse defined by position vector $\vec{p}$ and momentum vector $\vec{J}$ would be observed by a theoretical MCG sensor unit. Preferably, MCG sensor unit simulator 26 uses the Biot-Sarvart Law in the generating of second MCG image 16'.

Thus, FIG. 3 provides two basic methods of implementing the present invention. In one approach, MCG Image synthesizer 14 receives low-res first MCG image 12, uses high-res/low-res model fitting to generate high-res second MCG image 16 (i.e. fits low-res, first MCG image 12 to a high-res PCA linear model 22), and de-noise image processing block 18 generates low-res third MCG image 20 from the output of PCA linear model 22.

In an alternate approach, PCA model fitting+dipole reconstruction is used in the construction of de-noised low-res third MCG image 20. That is, electric current localizer 24 and MCG sensor unit simulator 26 provide dipole reconstruction to the output of PCA linear model 22, and de-noise image processing block 18 generates low-res third MCG image 20 from the output of MCG sensor unit simulator 26. This alternate approach may also be summarized as: given a restored 2D high-res MCG image (preferably, the output of PCA linear model 22), estimate the 2D location of the current, solve the inverse problem to reconstruct the 3D position and moment of the current dipole, and compute high-res second MCG image 16' given the reconstructed current dipole based on the Biot-Savart Law. In a preferred embodiment, de-noise image processing block 18 uses the corresponding 2D low-res components of high-res second MCG image 16' as de-noised MCG signals.

Some de-noise results obtained by the present invention are shown in the tables of FIGS. 4-6. The table of FIG. 4 compares de-noise results with ground truth in a simulation set-up with 8×8 sensors, 2.5 cm spacing, 200 trials, and each trial has normalize Bm and Bg to [0,1]. Using 25 modes, relative error is computed using:

$$\left(\frac{1}{200}\sum_{200}\frac{1}{64}\sum_{i}^{64}\left|\frac{\tilde{B}_m^i - \tilde{B}_g^i}{\tilde{B}_g^i}\right|\right) \cdot 100\%$$

As shown, both approaches render good de-noise measurements, but the method that using high-res model fitting followed by dipole reconstruction consistently provided better results.

Similar results are shown in the table of FIG. 5, uses a simulation setup of 8×8 sensors, 2.5 cm spacing, 200 trials with each trial having normalize Bm and Bg to [0,1]. Using 15 modes, the relative error is computed as:

$$\left(\frac{1}{200}\sum_{200}\frac{1}{64}\sum_{i}^{64}\left|\frac{\tilde{B}_m^i - \tilde{B}_g^i}{\tilde{B}_g^i}\right|\right) \cdot 100\%$$

In the above two simulations, when random noise is less than 20%, the embodiment using only model fitting (both high-res and low-res model) can reduce noise. However, by reconstructing the dipole, noise can be reduced even further.

The results of a phantom experiment are shown in the table of FIG. 6. This phantom experiment used 8×8 sensors, 2 cm spacing, a 4 turn vertical circular coil, and normalized Bm and Bg to [0,1]. Mean relative error is computed:

$$\left(\frac{1}{64}\sum_{i}^{64}\left|\frac{\tilde{B}_m^i - \tilde{B}_g^i}{\tilde{B}_g^i}\right|\right) \cdot 100\%$$

These results again show the both approaches demonstrate effective de-noise capabilities, but the approach using high-res model fitting followed by dipole reconstruction consistently again provides better results. Indeed, the present phantom experiment shows that when noise is really big (>35%), model fitting+dipole reconstruction still can reduce noise significantly.

Detailed descriptions of preferred methods of constructing and using high-res MCG image synthesizer 14 are provided below. Before discussing the detail descriptions, however, it may be beneficial to discuss an overview of some of its principles.

Figure 7:
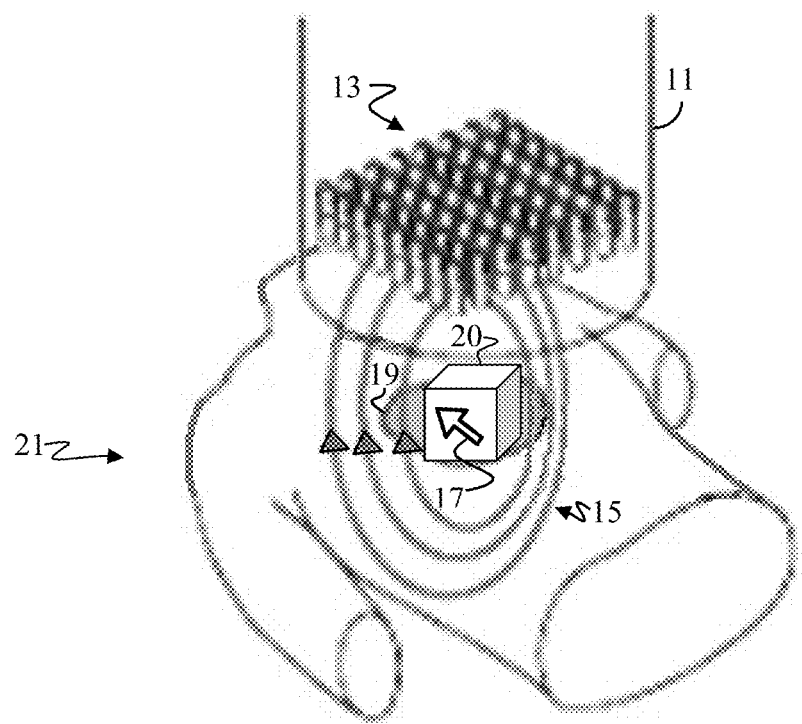
FIG. 7 illustrates a principle of the present modeling system.

FIG. 7 illustrates a principle of the present modeling case. All elements similar to those of FIG. 1A have similar reference characters and are described above. The basic principle is to simulate heart 19 as a block of heart tissue 20, and then to simulate a plurality of current impulses 17 within heart tissue block. Since the physical properties of heart tissue 20 is known, the propagation of a magnetic field through heart tissue 20 as generated by current impulses 17 can be simulated. The size of heart tissue block 20 may be of comparable size as heart 19 (or of similar volume as an average human heart).

Figure 8:
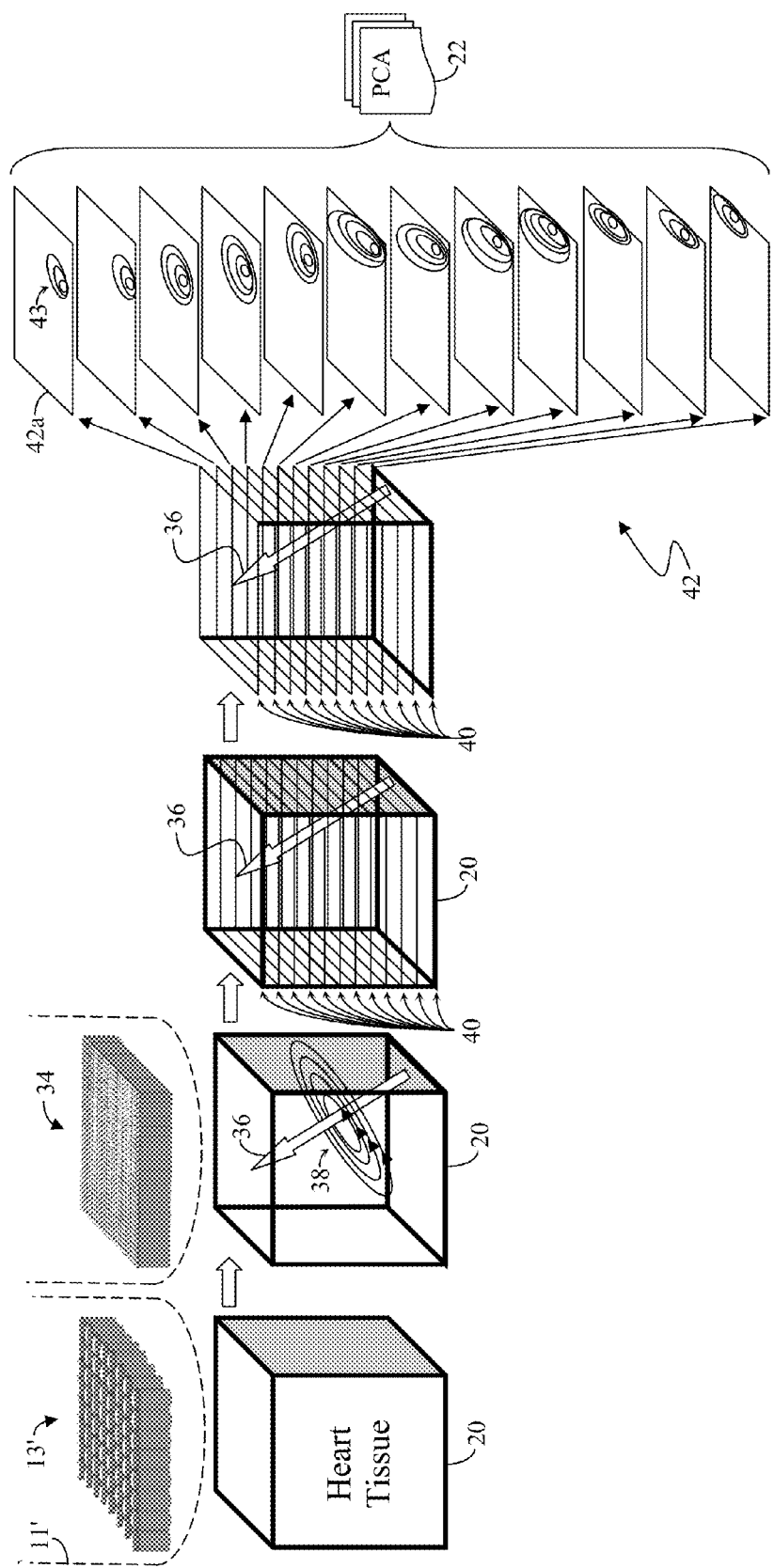
FIG. 8 illustrates additional principles of the present modeling system.

With reference to FIG. 8, a hypothetical MCG sensor unit 11' similar to MCG sensor unit 11 is of FIG. 1A is shown over heart tissue volume 20. Theoretical MCG sensor unit 11' could house a similar number of hypothetical electromagnetic sensors 13' as physical electromagnetic sensors 13 of FIG. 1A. This case, hypothetical MCG sensor unit 11' would be a low resolution MCG sensor unit, that of FIG. 1A. However, since in addition to removing noise, another objective of the present invention is to enhance the measurement readings from a physical MCG sensor unit, and since one is free to define the hypothetical MCG sensor unit to have any desired features, it is preferred that low resolution hypothetical MCG sensor unit 11' be replaced with a high resolution, hypothetical MCG sensor unit 32.

Hypothetical high-res MCG sensor unit 32 would have a similar resolution as high-res second MCG image 16 of FIG. 2, and thus would house a larger array 34 of hypothetical electromagnetic sensors, one per pixel of second MCG image 16. A random, current impulse 36 could now be defined within heart tissue volume 20, and its resultant magnetic field generated. High-res MCG sensor unit 32 would no make high resolution readings (i.e. generate high-def MCG images) of the magnetic field at various depths within heart tissue volume 20.

For practical reasons, it is preferred to generate high-res MCG images at a predefined, limited number of depths, or layers 40 within heart tissue volume 20. The individual layers can then be extracted from heart tissue volume 20, and separated to create individual high-def MCG images 42 for each depth level. It is to be understood that a multitude of random current impulses would be defined, their magnetic fields generated, and resultant level images created. In one embodiment, 1000 random current impulses are defined, and 1000 sample images are created per depth level. These simulated high-res MCG images 42 are then used to construct PCA-based, high-res MCG image model 22.

In this embodiment, the area covered by hypothetical high-res MCG sensor unit 32 is the same as the area covered by hypothetical low-res MCG sensor unit 11'. That is, the physical sensor area hypothetical high-res MCG sensor unit 32 matches that of hypothetical low-res MCG sensor unit 11', which in turn, matches that of physical low-res MCG sensor unit 11.

However, a larger MCG sensor unit would likely provide larger images and thus more information with which a medical profession could work. Since it is costly to create larger physical MCG unit, and impossible to create a larger, physical high-res MCG sensor unit, the present alternate embodiment modifies hypothetical high-res MCG sensor unit 32 to simulate a larger-sized high res MCG sensor unit.

Figure 9:
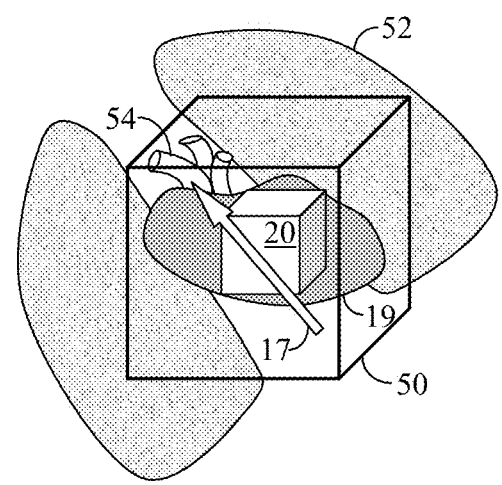
FIG. 9 illustrates one implementation of an expanded model in accord with the present invention.

With reference to FIG. 9, with all elements similar to those of FIG. 7 have similar reference characters and are described above, large model block 50 encompasses previous heart tissue block 20. As an example, model block 50 may be twice as long and twice as high as heart tissue block 20. In one example, model block may constitute a solid heart tissue mass similar to that of heart tissue block 20, but of larger size and can thus simulate larger-sized hearts, or as a second example, provide a fuller model of heart 19.

In an alternate third example, model block 50 may be made to span beyond the heart tissue of a typical heart. In this third example, model block 50 may be modeled to represent a 3D representation of the different types of tissue masses it encompasses. Thus, in addition to the heart-shape tissue mass within its center representing hear 19, model block 50 may optionally model heart arteries 54, lungs 52, and any other tissues within its volume.

In these three examples, larger model block 50 provides for a better view of the magnetic field generated by a random impulse current 17. It is further noted that irrespective of whether model block 50 is modeled as a heart tissue mass, or as a combination of different adjoining tissues masses, the general process for generating a PCA linear model is similar that described generally above, and in more detail below.

Figure 10:
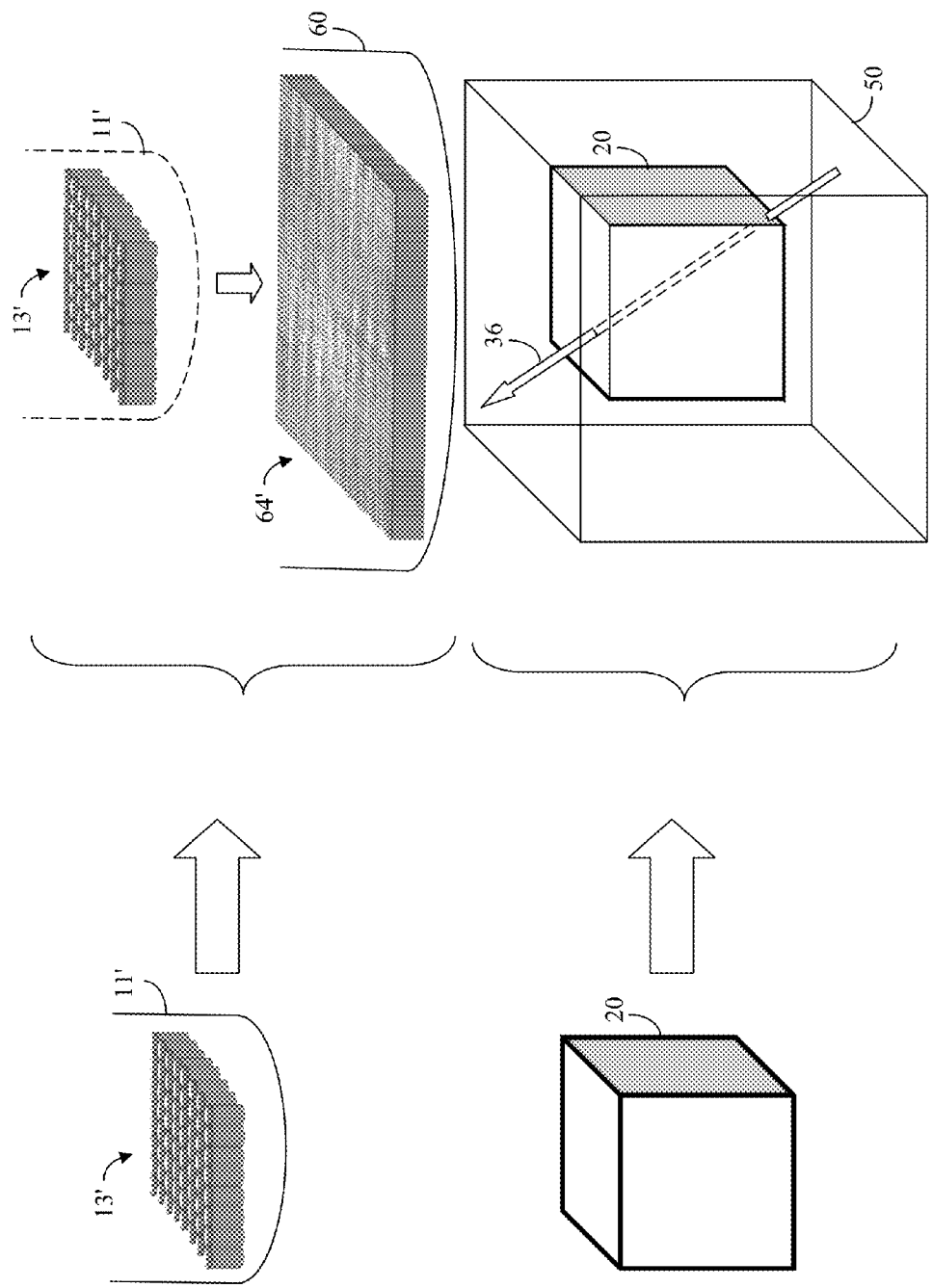
FIG. 10 illustrates a principle of the present expanded model.

For example in FIG. 10, where all elements similar to those of FIGS. 8 and 9 have similar reference characters and are described above, hypothetical low-res MCG sensor unit 11' is replaced with a larger hypothetical high-res MCG sensor unit 60 having an imaging area larger than the sensor area of low-res MCG sensor unit 11'. The density of electromagnetic sensors per unit area of array 64 is preferably the same as that of array 34 of FIG. 8. The sensor area of array 64 of electromagnetic sensors is defined by the top face area of model block 50. As stated before, model block 50 is preferably twice as wide and twice as high as heart tissue block 20.

Before presenting some experimental, de-noising results obtained by the present invention, it may be beneficial to provide more detailed, exemplary implementations of the above-described high-res MCG image synthesizer 14. More specifically, it may beneficial to present preferred implementations of PCA linear model 22, electric current localizer 24, and MCG sensor unit simulator 26.

As it may be understood, a collection of high-res 2D MCG images at increasing depths levels may be combined to create a three-dimensional (3D) MCG image. Thus, a high-res generating method/process/device that improves the accuracy of high-res 2D MCG images could be used to create a three-dimensional (3D) construct of position, magnitude and orientation of electric currents from a given set of low-res MCG measurements. One method that provides for improved accuracy computes high-res MCG images based on electric currents determined by means of the Biot-Savart law. As it is known in the art, however, according to the Helmboltz reciprocity principal, the inverse problem for MCG is an ill posed problem unless the number of electric impulses is known. But even when the number of electric impulses is known, it requires solving a large scale nonlinear optimization problem that is often computationally expensive and may lead to undesired local minima. Therefore, high-res MCG image restoration (i.e. generation) based on these types of methods have previously been unreliable.

The presently preferred embodiment considers the high-res MCG image restoration (i.e. generation) problem as an exemplar-based super-resolution problem. Typically, exemplar-based problems require a library of true examples (i.e. true sample images) from which to learn characteristics of such true examples. However, it is impractical, if not impossible; to measure dense magnetic fields, and thus it is not feasible to obtain such true examples from directly observed true measurements. Therefore, the presently preferred embodiment uses computer-generated (i.e. synthetic) high-res MCG images as the library of true sample images for training purposes. That is, the present model learning algorithm is based on synthetic high-res MCG images.

The synthetic high-res MCG images that comprise the present library of sample images are preferably randomly generated based on the Biot-Savart Law. From these sample images, a linear model is constructed, preferably by use of principal component analysis (PCA). Sparse, true measurements from a physical MCG sensor unit are then projected into the subspace of the thus-constructed linear model to estimate model coefficients and restore (i.e. create, synthesize or generate) a high-res MCG image as a model instance of the linear model. This model instance may be output as a high-res MCG image representation of the low resolution image defined by physical MCG sensor's spare measurements.

With the high-res MCG image thus reconstructed, the presently preferred invention preferably further analyzes the high-res MCG image to identify the location, depth, magnitude and orientation of an electric impulse current that would produce such an image.

As is explained above, true MCG images obtained from observed physical measurements are typically comprised of low-res, 2D MCG maps that do not provide enough information for directly recovering specific electric impulse current information. However, once the high-res MCG image is reconstructed, the 2D position of the electric current can be localized as the maximal point of the tangential components of the high-res MCG image. To improve the 2D localization accuracy, a nonlinear optimization algorithm is herein described to solve the inverse problem. At the same time, the depth, magnitude and orientation of the electric current are also recovered. More specifically, the preferred algorithm iteratively alternates between two steps. The first step estimates the originating position of 3D electric impulse current, and the second step reconstructs its magnitude and orientation based on the estimated originating position. In the estimating of the originating position of 3D electric impulse current, the 2D current location estimated from the model based restoration is used as the initialization. The present method is efficient, accurate and reliable without the need of special assumptions. For the sake of simplicity, the presently preferred system/method is illustrated as applied to a single electric impulse current case only. It is to be understood, however, that extension of the present system/method/device to multiple impulse currents is straightforward.

The present embodiment utilizes various computing devices (or data processing devices) to learn (i.e. create) a linear model from a set of synthesized high-res MCG images generated by random electric impulse currents. Sparse data (i.e. a low resolution image) received from an MCG sensor unit is then projected onto the linear model, and a high resolution image representation of the low resolution image is created there from. An example of this approach is illustrated in FIG. 11.

Figure 11:
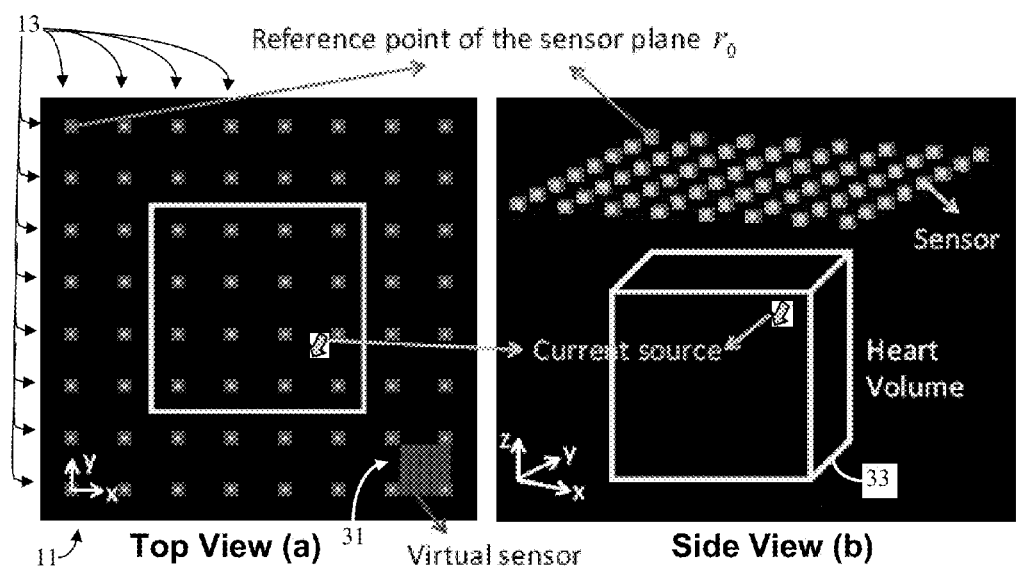
FIG. 11 illustrates a 2D sensor array in spatial relation with a heart volume in a simulation setup in accord with the present invention.

With reference to FIG. 11, Top View (a) illustrates a top-view of a 2D sensor array (or sensor plane) in relationship to a side-view, 3D spatial heart volume 33 [Side View (b)] in a simulation setup. In the present example, Top View (a) illustrates a top view of an MCG sensor unit (such as MCG sensor unit 11 of FIG. 1A) with 64 physical sensors 13 (such as electromagnetic sensors 13) arranged in an 8×8 sensor array. In the present embodiment, however, a set of four virtual sensors 31 are inserted in-line between adjacent real, physical sensors 13 in the x- and y-directions. Additionally, the square area defined by four corner physical sensors 13 and their four aligned sets of virtual sensors 31 is filled with a 4×4 array of additional virtual sensors 31. Thus, the present embodiment adds 1232 virtual sensors 31 to the 64 physical sensors 13 for a total of 1296 sensors. This is equivalent to a 36×36 sensor array, and constitutes the basis for one embodiment of the present high-res image. Assigning one image pixel per sensor, the present embodiment thus provides for P×P (P>8) pixels in a high-res MCG image. Preferably, the sensor plane is 5 to 10 cm above the heart volume bounding box 33, which in the present case is 10×10×10 cm³. In this example, the pixel density in each high-res MCG image would be (1296 pixels)/(100 cm²), or about 13 pixels per square centimeter. The electric current is represented by a vector located at a 3D point.

It is to be understood that the number of virtual sensors, and thus the value of P is a design choice. A later embodiment described below, for example, incorporates a higher number of virtual sensors to produce an even higher resolution MCG image.

FIGS. 18A to 18C show various equations (Eq. 1 to Eq. 12) to facilitate discussion.

Given a single electric current, a resultant magnetic field at each sensor can be computed based on the Biot-Savart Law, equation Eq. 1, where $\vec{J}(\vec{p})$ is the moment of the electric current including its magnitude and orientation. In this case, $\vec{p}$ is the 3-dimensional (i.e. 3D) position vector of the electric current. Note that this representation of electric current is an approximation by assuming the size (or magnitude) of the current is zero. One can consider that the volume (size, or density) information is included in the moment vector $\vec{J}$. $\vec{B}(\vec{r}_m)$ is the magnetic vector measured by the $m_{th}$ sensor at position $\vec{r}_m = \vec{r}_o + \vec{\delta}_m$, where $r_o$ is the reference point of the sensor plane and $\delta m$ indicates the offset of the $m_{th}$ sensor with respect to $r_o$. As it would be understood, $\mu_o$ is the magnetic constant.

As it is known in the art, typical MCG systems are capable of measuring only the z component of $\vec{B}$. Thus, to simulate MCG system measurements, one needs to determine the z components of a simulated $\vec{B}$.

From Eq. 1 one may compute $B_z$ (the z component of $\vec{B}$) by means of equation Eq. 2, where $J^1$, $J^2$, $J^3$ represent the three components of the current moment vector $\vec{J}$; $x_p$, $y_p$, $z_p$ represent the three components of the current position vector $\vec{p}$; and $r_m^1$, $r_m^2$, $r_m^3$ represent the three components of the sensor position vector $\vec{r}_m$.

In a training step, a set of high-res P×P MCG images (where P>>M) are synthesized, i.e. generated. To generate each high-res P×P MCG image, a single electric current with both random moment and random 3D position is defined. The resultant high-res P×P MCG image is computed based on Eq. 2.

Figure 12:
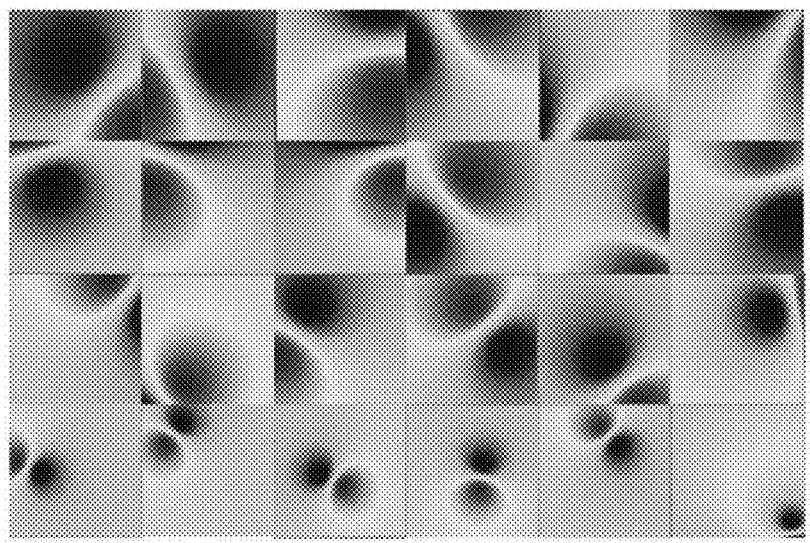
FIG. 12 shows various examples of training images in accord with the present invention.

Some examples of synthesized training images are shown in FIG. 12. Each synthesized high-res MCG image is generated by a single electric current with both random moment and 3D position. Since the magnetic field generated by the heart is very weak ($10^{-12}$ to $10^{-10}$ Tesla), the high-res MCG image is normalized to 0~255 and displayed using a JET color map. The images from different rows are generated from different depths (the distance of the electric current in the z direction). In this manner, K high-res MCG training images are generated, i.e. synthesized. All the image vectors are centralized (the mean vector is denoted by $\mu$), and they are stacked into a matrix A. Matrix A thus consists of K columns of P×P vectors. PCA is applied to extract the eigenvectors of matrix A, and thus define an eigenmatrix $\Sigma$.

A received sparse M×M MCG image, as measured by an MCG sensor unit, defines a vector g. To restore (i.e. create or define) a high-res MCG image representation of the given sparse M×M measurements (vector g), one first extracts from the eigenmatrix $\Sigma$ the rows corresponding to the rows defined by the M×M measurements to form a sub-eigenmatrix $\Sigma g$. Similarly, vector g's corresponding elements from mean vector $\mu$ form a sub-mean vector $\mu_g$. Vector g is then projected to sub-eigenmatrix $\Sigma g$, and model coefficients $c_g$ are calculated as $c_g = \Sigma_g^+ (g_j - \mu_g)$, where $\Sigma_g^+$ is the pseudo inverse of $\Sigma g$. Finally the original eigenmatrix $\Sigma$ along with estimated coefficients $c_g$ are used to construct a high-res MCG image vector h, as $h = \Sigma \cdot c_g + \mu$, where h is a P×P vector.

FIG. 12 illustrates four rows of different MCG images (i.e. four 2D MCG images). The four rows of MCG images are generated at four respective depths, or layers, (i.e. different distances to electric current locations, or sources, in the z direction). A big variance can be seen between the MCG images when changing depths.

Figure 13A:
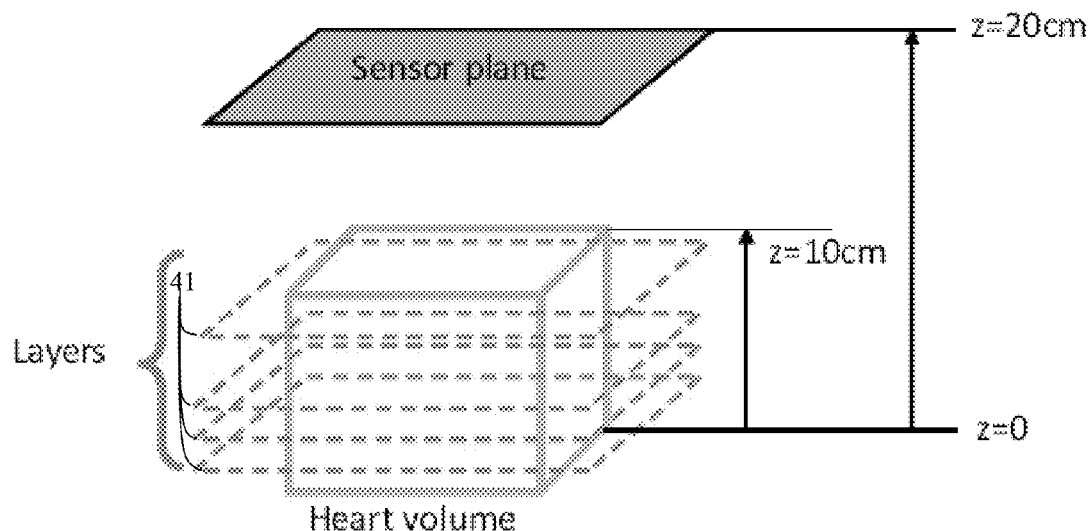
FIG. 13a illustrates the random generation of electric currents at different depth layers.

An illustration of these depth layers 41 is shown in FIG. 13A. In the presently preferred embodiment, electric currents are randomly generated at different depth layers 41. It would be too exhaustive to sample every depth to select a set of depth layers. This approach assumes that $B_z$ can be approximated as a linear function of the current depth, as is explained more fully below.

In the present approach, the sensor positions $\vec{r}_m$, the 2D position $(x_p, y_p)$, and the moment $\vec{J}$ of the electric current are fixed. $B_z$ is only affected by the depth z of the current. Thus, Eq. 2 can be simplified to Eq. 3, where $a_m$ and $b_m$ are constants but unknowns, c=20 cm is the depth of the sensor, and z is the depth of the current, which varies between 0 to 10 cm within the heart volume bounding box. Preferably, $a_m$ lies in a range from −7.5 to 7.5 cm, and $b_m$ lies in a range from 0 to 112.5 cm.

By applying Taylor expansion to Eq. 3, one obtains Eq. 4. By ignoring $O(\Delta z^3)$, one only needs to prove that $$\frac{d^2}{2dz} B_z^m(z)$$

is close to zero for any possible z and any sensor.

Figure 13B:
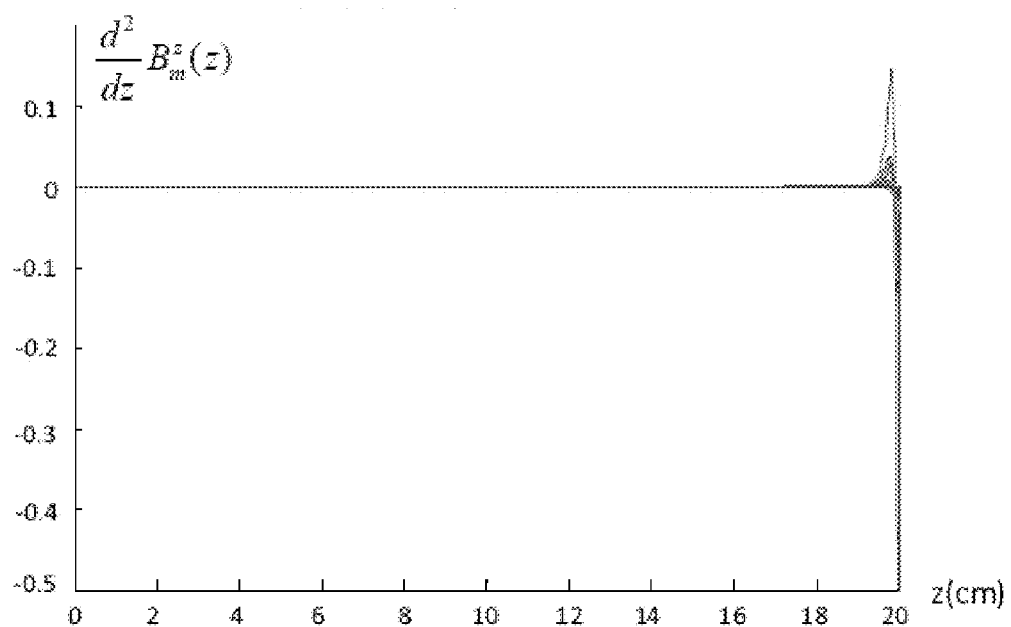
FIG. 13b plots the results of 64 trials at different depths, z.

A graph of $$\frac{d^2}{2dz} B_z^m(z)$$

versus depth, z, is shown in FIG. 13b. More specifically, the graph shows $$\frac{d^2}{2dz} B_z^m(z)$$

in 64 trials with random $a_m$ and $b_m$ in each trial. As shown, $$\frac{d^2}{2dz} B_z^m(z)$$

demonstrates a very small value (close to zero) when z varies from 0 to 10 cm. Therefore, a set of depth layers was sampled within this depth range, as is illustrated in FIG. 13a.

In the present example, one thousand high resolution MCG image samples were generated in each of 10 evenly distributed depth layers, or levels.

Figure 14:
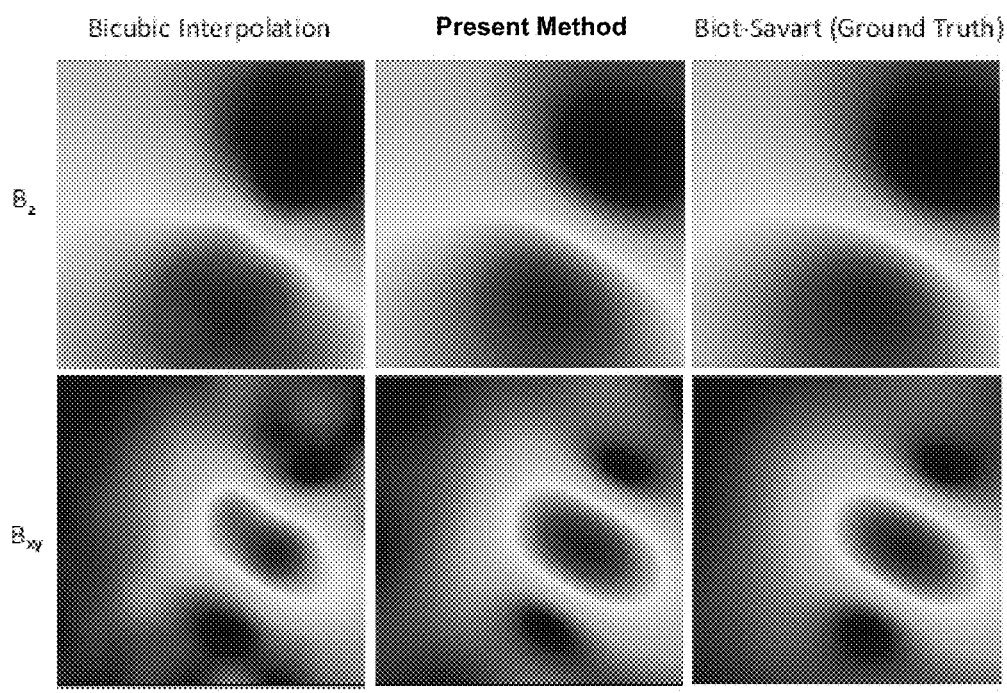
FIG. 14 compares high-res MCG images creating using the present invention with a prior art method and with a ground truth example.

The Bz view and Bxy view of the presently preferred method of creating a restored high-res MCG image was then compared with the bicubic interpolation method, as well as with the ground truth images, as is illustrated in FIG. 14. For evaluation purposes, a high-res MCG image reconstructed from the ground truth current based on the Biot-Sarvart Law is shown. To better simulate physical conditions, 5% uniformly distributed random noise was added to each sensor, and the presently preferred method as well as the bicubic interpolation method were then applied to the noisy sensor results. As is visually evident from the side-by-side comparison of the three images, the high-res MCG image constructed by means of the presently preferred method more closely matches the ground truth MCG image. Thus the present method achieves a higher level of accuracy in constructing high-res MCG images.

As is mentioned above, a 2D estimate of the electric current location can be obtained by analyzing the high-res MCG image. A presently preferred method for improving the localization accuracy is to solve a nonlinear optimization that reconstructs both 3D position and moment of the electric current, i.e. the inverse problem. An accurate high-res MCG image restored by the linear model provides a good initialization for the inverse problem and helps it converge on the global optimum more quickly. The preferred method for generating a 2D estimate from a high-res MCG image is as follows.

Given a high-res MCG image $B_z(i,j)(i=1, 2, \ldots, N; j=1, 2, \ldots, N)$, the maximal point of the tangential components $B'_{xy}(i,j)$ of $B_z(i, j)$ refers to the 2D position $(x_p, y_p)$ of the electric current. This may be seen in the second row images of FIG. 14. The tangential components of $B_z(i,j)$ may be computed using equation Eq. 5. One now is left with solving the inverse problem.

Figure 15:
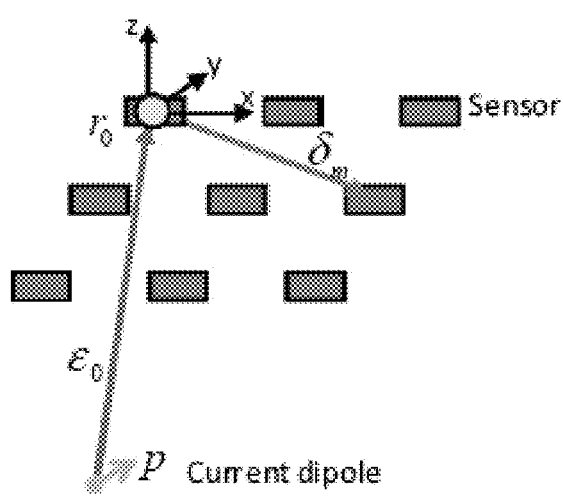
FIG. 15 illustrates the spatial configuration of sensors and electric current in accord with the present invention.

The inverse problem is to solve both 3D position $\vec{p}$ and moment $\vec{j}$ of the electric current. This approach may be better understood with reference to FIG. 15, where $\vec{r}_o$ is set as the world origin. If $\vec{p}$ is given, the inverse problem becomes a linear one. First, Eq. 1 may be rewritten as Eq. 6, where $\vec{B}^m = \vec{B}(\vec{r}_m)$, $\vec{J} = \vec{J}(\vec{p})$, and $$\vec{R}_m = \frac{\mu_O}{4\pi} \frac{(\vec{r}_m - \vec{p})}{\|(\vec{r}_m - \vec{p})\|^3}.$$

Eq. 6 is then expanded to a matrix form by using a skew symmetric matrix, which results in Eq. 7 of FIG. 18B. In this case, the z component of the magnetic field can be computed as shown in Eq. 8, where $R_m^1, R_m^2$ are x,y components of $\vec{R}_m$. Given M sensors, a linear system is defined as illustrated in equation Eq. 9, where B is a measured M×1 vector, R is a M×2 position matrix that is computed from given $\vec{p}$ and $\vec{\delta}_m$. In the present case, J is a 2×1 unknown vector. When rank(R)≥2 (this holds for the single electric current case with 64 sensors), one can solve a least square solution for J, as illustrated in equation Eq. 10.

Note that by only measuring $B_z$ it is impossible to recover $J^3$. In fact, the magnetic field generated by the z component of the current only propagates along the horizontal direction and never reaches outside of the body. For the following computation, one sets $J^3=0$. Given an estimated current moment $\vec{J}=[J,0]$, one can update the current position $\vec{p}$.

Eq. 1 is rewritten as equation Eq. 11. One may then let $a=4\pi/\mu_0$ and $\vec{\epsilon}_o=\vec{r}_o-\vec{p}$. $\vec{\delta}_m$ is known for each sensor. One may then apply equation Eq. 12 to obtain $a\vec{B}^m$. In Eq. 12, let $\vec{\tau}_m=\vec{J}\times\vec{\delta}_m$ and $\vec{\epsilon}_o=(x_\epsilon, y_\epsilon, z_\epsilon)^T$. It is noted that $\vec{\tau}_m$ can be computed given $\vec{J}$. Again, the cross product is removed from Eq. 12 by using a skew-symmetric matrix. Therefor for each sensor m=1: M, one obtains a nonlinear equation in terms of $(x_\epsilon, y_\epsilon, z_\epsilon)$, as illustrated in Eq. 13. Letting $F=(f^1; f^2; \ldots; f^M)=0$, one then solves a least square solution of the nonlinear system F for $\vec{\epsilon}_o$.

Once the offset $\vec{\epsilon}_o$ is obtained, the position matrix R can be updated and J can be recomputed. These iterations are repeated until the algorithm converges. The inverse problem step converges in real time (0.5 seconds on average). Finally $\vec{p}=\vec{r}_o-\vec{\epsilon}_o$. Since the high-res MCG image only provides an estimate for 2D current position $(x_p, y_p)$, the initial depth z and magnitude $\|\vec{J}\|$ of the electric current are given by equation Eq. 14, where d is the distance between two magnetic poles in the high-res MCG image.

The present high-res MCG image restoration method and electric current localization algorithm was evaluated using both simulations and physical phantom setups. In both scenarios the ground truth of the 3D position $\vec{p}_g$ and moment $\vec{J}_g$ of the electric current are known.

The present simulation setup is similar to the setup shown in FIG. 1A. There are 8×8 physical sensors 13 with a 2.5 cm sensor interval. The entire measuring area is 17.5×17.5 cm². The heart volume 19 is 10×10×10 cm³. The distance from the sensor array (or sensor unit) 11 to the top of the heart volume 19 is 5 cm. In each trial, a random electric current within the heart volume is generated. $B_z$ is computed at the 64 sensors 13, and 5%, 10% or 15% random noise is added to each sensor. This added noise has a uniform or Gaussian distribution. The 64 sparse measurements with noise are used to restore a high-res MCG image having an N×N resolution. To achieve this, 50 pixels are inserted between two adjacent real sensors, which means that the interval between adjacent pixels in the high-res MCG image is 0.5 mm. In this case $N=50\times 7+1=351$.

Tables 1 to 4 in FIGS. 19a to 19d, respectively, illustrate some simulation results. Table 1 in FIG. 19a shows the 2D electric current localization error with respect to different noise types and ratios over 200 trials (depth is not considered in this case). There are a number of previous works that report accuracy about the 2D electric current localization. For example, "Biomagnetic Noninvasive Localization of Accessory Pathways in Wolff-Parkinson-White Syndrome", in *Pacing and Clinical Electrophysiology*, by Weismuller et al., 14(111):1961-1965, 1991, and in "Magnetocardiographic Non-invasive Localization of Accessory Pathways in the Wolff-Parkinson-White Syndrome by a Multichannel System", in *European Heart J.*, by P. Weismuller and et al, 13(5):616-622, 1992, the 2D localization accuracy for Wolff-Parkinson-White (WPW) syndrome is between 0 cm to 5 cm, and average 1.8 cm. Also, "Magnetocardiographic Localization of Arrhythmia Substrates: a Methodology Study with Accessory Pathway Ablation as Reference", in *IEEE Trans. on Medical Imaging*, by P. L. Agren and et al., 17(3):479-485, 1998, reports the 2D localization accuracy for arrhythmia substrate as being 2.1 cm and 9.6 cm. Lastly, "Noninvasive Diagnosis of Arrhythmic Foci by Using Magnetocardiograms, —Method and Accuracy of Magneto-Anatomical Mapping System", in *J. of Arrhythmia*, by S. Yamada and et al., 16:580-586, 2000, and "Magnetocardiograms in clinical medicine: unique information on cardiac ischemia", by S. Yamada et al., in *Arrhythmias and Fetal Diagnosis*, 2005, show a similar setup consisting of 8×8 sensors, a 2.5 cm sensor interval, and a 5% random noise, but neither the sensor depth nor the noise type is reported. They report the 2D localization accuracy as being 1.4 mm+/−0.7 mm for simulation, 8 mm for WPW and 7 mm PCV. Compared to previous work, the method shows better accuracy than the current state of art.

Moreover, since the present method solves the inverse problem, the present method permits the reconstruction of the 3D position of the electric current and its moment. Applicants believe that the present ability to reconstruct a 3D current is new to the present field.

Table 2 in FIG. 19b shows the 3D current localization error. When the noise level is increased, the depth reconstruction becomes less accurate, which can be caused by an inaccurate initialization. Table 4 in FIG. 19d shows the orientation difference between the reconstructed current moment $\vec{J}_{rec}$ and the ground truth current moment $\vec{J}_g$. As can be seen, the orientation of the electric current is very robust to not only the measurement noise, but also the depth error.

Figure 16:
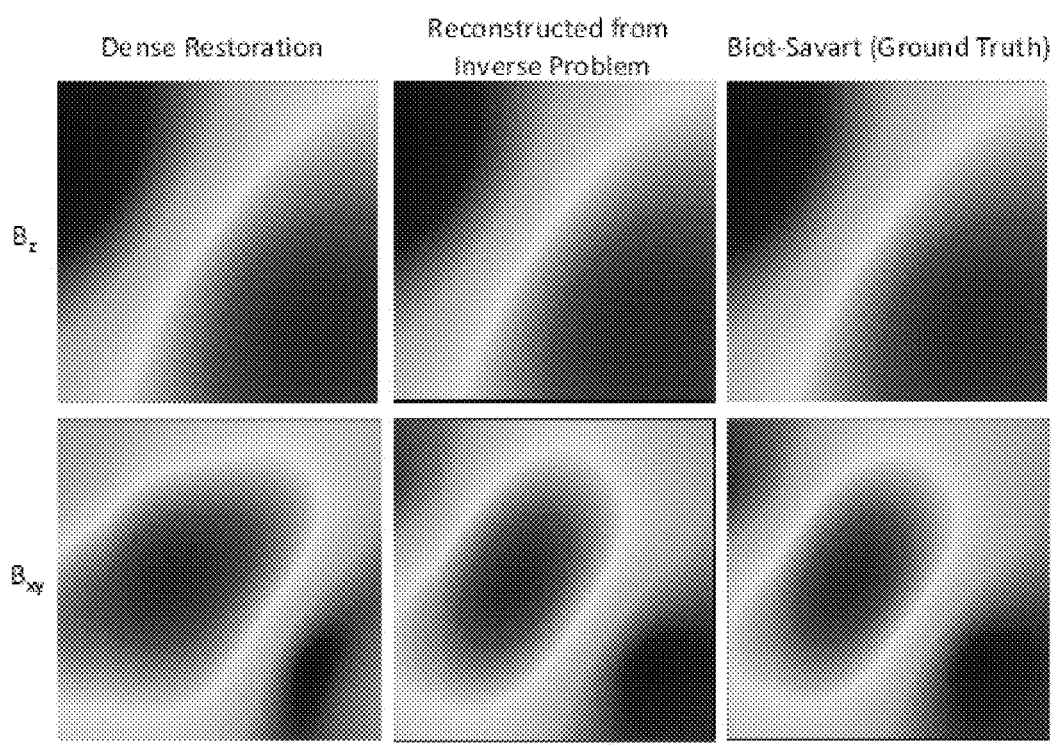
FIG. 16 compares high-res MCG images creating using the present invention with a prior art method and with a ground truth example.

Table 3 in FIG. 19c shows the current magnitude reconstruction error. Since the current magnitude is very weak, the relative error is computed. All the results are averaged from 200 trials. FIG. 16 shows an example of a high-res MCG image restored by the linear model(left), a high-res MCG image computed given the reconstructed current $(\vec{J}_{rec}, \vec{p}_{rec})$ (middle), and a high-res MCG image computed given the ground truth current $(\vec{J}_g, \vec{p}_g)$ (right), and 5% uniformly distributed random noise is added to each sensor.

Figure 17:
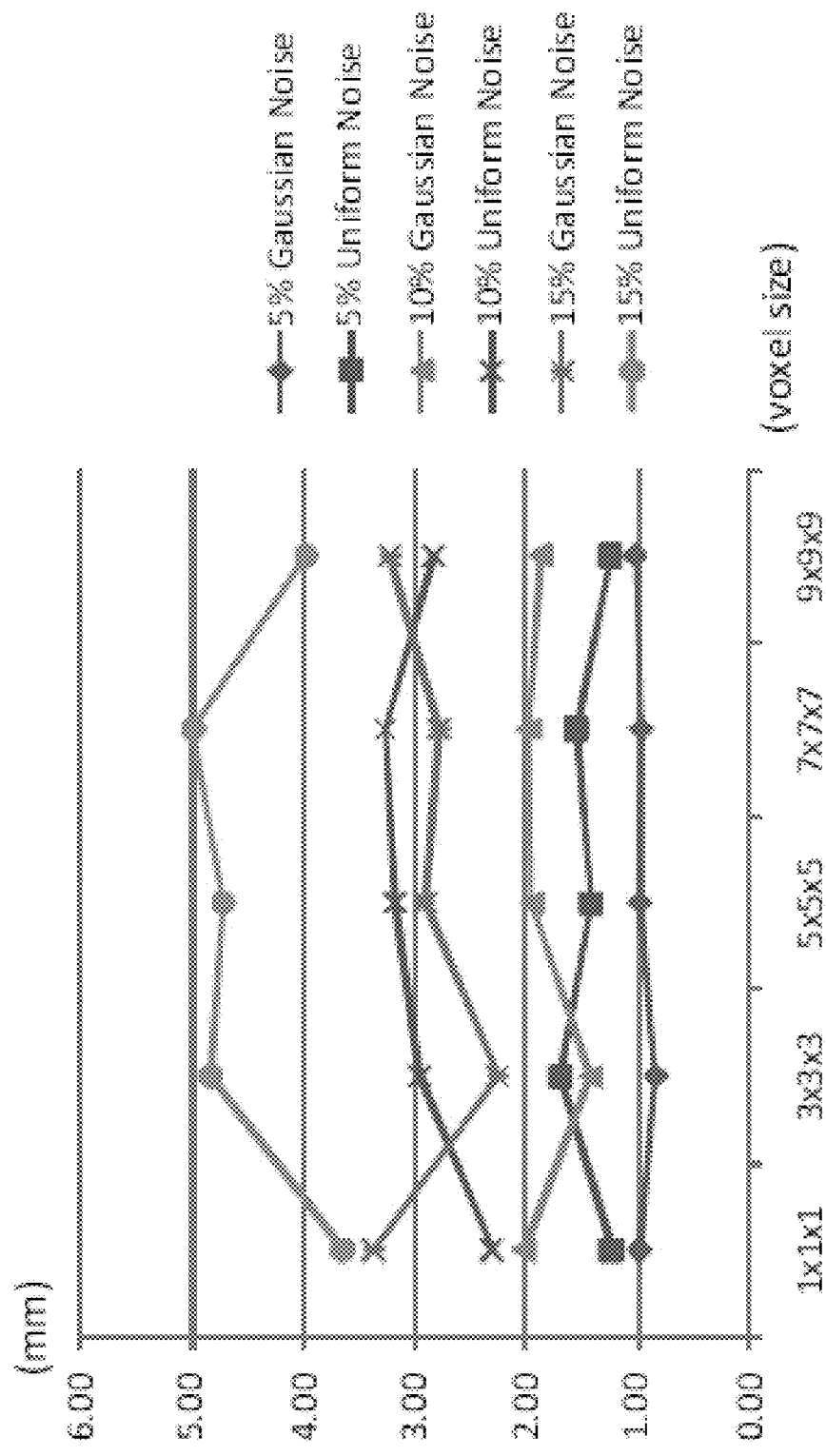
FIG. 17 illustrates 2D voxel current localization errors with respect to different the size of voxel current.

In reality, an electric current is more like a voxel rather than a point. Different sizes of voxel currents were simulated by generating a set of point currents within a small cube by a 0.5 mm interval. FIG. 17 shows the 2D localization error for voxel currents. The geometric center of the voxel current is used as the ground truth. The results demonstrate that the present localization algorithm is robust to the size of the electric current, and comparable to the state of art (which only considers the point current).

Hereinabove, only the single electric current localization problem is considered, and a good initialization can be computed from the dense MCG image. In reality there can be more than one electric voxel current. Signal decomposition might be needed for initialization of the multiple current localization. In summary the present method is capable of restoring/creating accurate high-res MCG images. The high-res MCG images are created in an efficient, accurate and reliable manner for single current 2D localization. In addition the present algorithm can reconstruct the depth and moment of the current. It can also be easily extended to solve for multiple current sources.

Figures 20, 21:
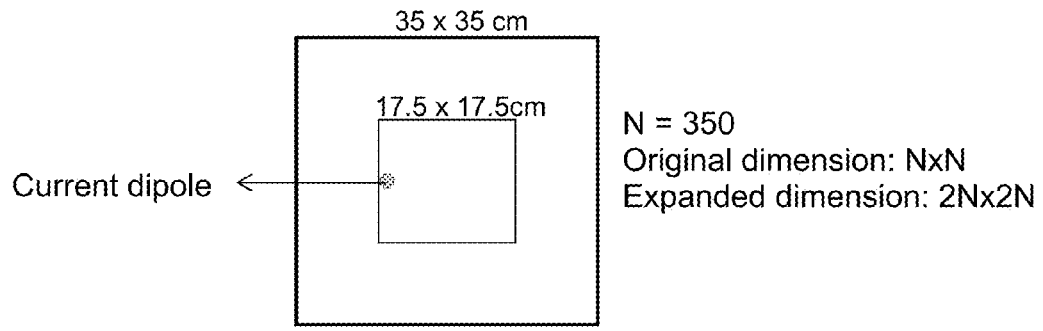
FIG. 20 illustrates how the expanded model provides more support for the current dipoles located on what is the boundary in the original model.
FIG. 21 illustrates how the extended dense magnetic field image of the expanded model may be computed and stored as a row vector $f_1^t$.

As is explained above, an alternate embodiment expands the sensor area of the original size spatial volume cube, preferably to 2×2 times of original size. For ease of discussion, the unexpanded implementation is hereinafter term the "original model", and the expanded implementation is termed the "expanded model". The original model is preferably expanded to create the expanded model by inserting virtual sensors outside of the sensor area. This provides more support for the current dipoles located in the boundary as illustrated in FIG. 20. Some advantages of this approach are: better visualization for diagnosis and localization, option for changing resolutions (i.e. zoom in), and better accuracy for boundary sources.

This approach, however, poses some practical challenges to its implementation. Firstly, it has high data storage and computation requirements. To overcome these practical limitations, the above described implementation of the expanded model may be modified to accommodate situations where computing resources are limited.

First, the extrapolation PCA model is learned from synthesized expanded high resolution MCG images, as explained above. That is, instead of using the original size of the sensor area, an expanded dense MCG image is computed for each sample. Secondly, long-term storage (i.e. hard disk space) may be use in place of active memory (i.e. RAM) to reduce active memory requirements. Finally, computation for model learning is divided and run in parallel, which significantly improves the execution time.

First, the computation for model learning is divided in preparation for execution in parallel. Given a random current dipole, the extended dense magnetic field image is computed and stored as a row vector $f_i^t$, as illustrated in FIG. 21. This step is repeated K times, and the K row vectors are stored in the data file as shown. In the above-described, original model, sample vectors in a row were generated, but in this alternate implementation, sample vectors are generated in threads. Preferably, 8 threads are generated for 8 CPUS. The resultant eight files are then merged into one.

With reference to FIG. 22, in implementation of the above-described original model, a memory buffer may be allocated for the data file and all may be read in at once to a matrix (72). The mean vector and normalized data matrix may then be computed (74). A memory buffer for the covariance matrix may then be allocated (since K<<2N×2N), (76). Eigen-decomposition may then be applied to the covariance matrix.

By contrast in the present implementation of the expanded model, The mean vector may be computed by reading the data vectors one by one and storing a mean vector in a hard disk. The covariance matrix may then be divided into L×L blocks (78). To compute each block, one may read the corresponding two blocks of sample vectors from the data file (for example blocks $b_1^t b_1$ or blocks $b_1^t b_L$ or blocks $b_L^t b_L$, etc.). Thus there is no need to store the entire data file in active memory. Further advantageously, this permits parallel computing of different blocks of the covariance matrix.

Figure 23:
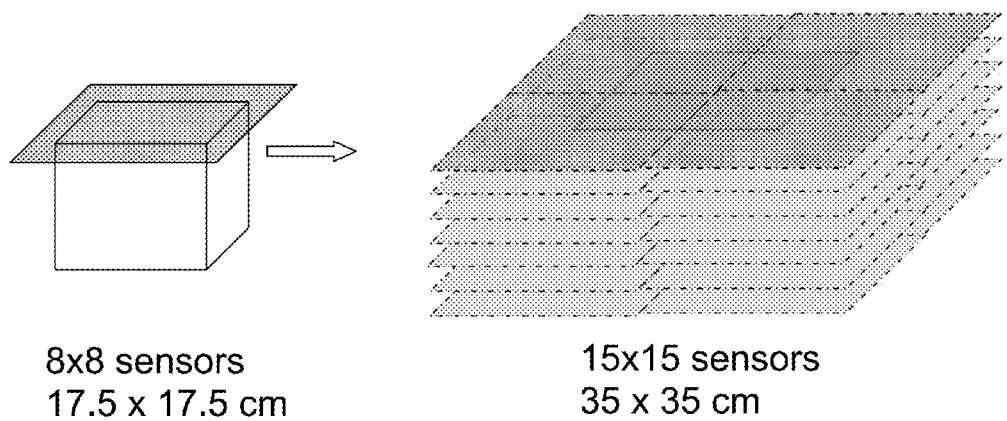
FIG. 23 illustrates an implementation of the expanded model.

An exemplary implementation of this is shown in FIG. 23. Random samples are generated in different horizontal planes within the expanded bounding box. In one embodiment, 2000 samples are generated, and preferably 6 horizontal layers with 2 cm spacing are defined. Random current impulses with random position and directions are generated, and their magnitude is normalized.

The efficiency improvement of the present implementation of the expanded model versus the original model was demonstrated by comparing experimental results. The original model was implemented in a 32 bit system, using a data scale of 12000 samples, 1G of active memory for the covariance matrix, and 1G of active memory for the data matrix. Processing time for this setup was about four weeks.

The expanded model was implemented using a 64 bit system with parallel computing. This implementation used a data scale of 60000 samples and 15G of active memory for the covariance matrix. Processing time (i.e. training time) for this alternate implementation was 6 days.

Besides providing a larger viewing area, the expanded model also demonstrated improved location accuracy. Using the original model, localization accuracy for a 1×1×1 voxel dipole, over 200 trials and 5% uniform noise, resulted in a value of 1.2+/−1.1 (mm). By contrast, the expanded model resulted in a value of 1.14+/−0.98 (mm).

Figure 25:
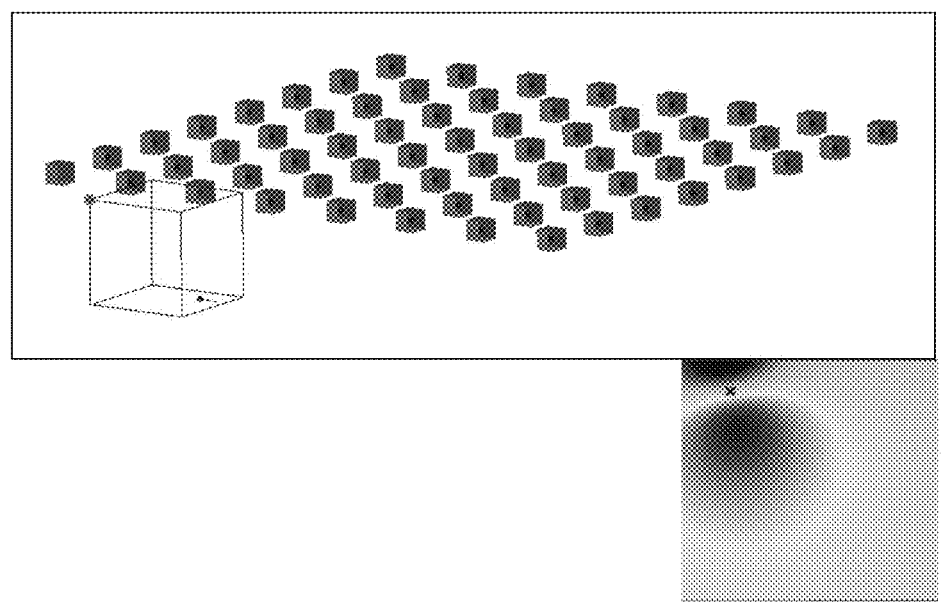
FIGS. 24 and 25 illustrate an experimental implementation of an embodiment of the present invention.
Figure 24:
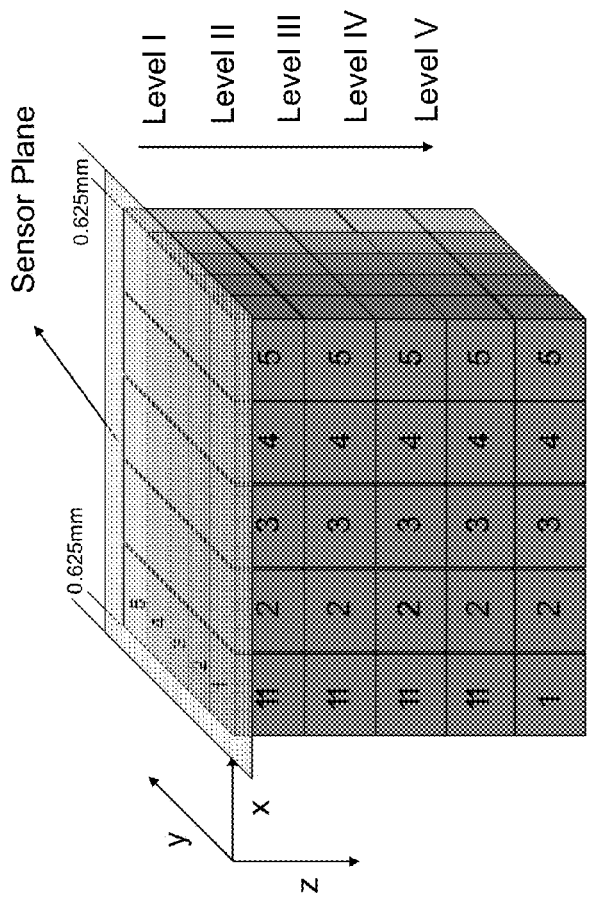

The dipole location error distribution in 3D space for the expanded model was also examined. This setup used 8×8 sensors, 2.5×2.5 cm spacing, 5% uniformly distributed noise, 3.25×3.25×3.25 measurement bounding cube, 1×1×1 3D voxel double layer source, a sensor offset set equal to bounding cube_z+1.25/2+0.25 (offset)=4.125 cm (for the top level), 5×5×5=125 measurement, and 100 trials in each measurement. The results of this experiment show that on average, the expanded model provides better localization accuracy for the current sources, especially for those located close to the sensor boundaries. Illustrations of this experiment are shown in FIGS. 24 and 25.

A comparison of measurement results for the original model and the expanded model for each of levels I through V are shown in FIGS. 26-30, respectively. In each of the tables for levels I through V, the X-Y coordinates correspond to the X-Y coordinates in FIG. 24, and the level number I though V correspond to the Z coordinate in FIG. 24. Also in each of the tables in FIGS. 26-30 for each row comparing the original model to the expanded model (numbered 1 to 5), the top number is the value obtained with original model and the bottom, larger font and bold-print number is the value obtained with the expanded model. As shown, most of the values obtained with the expanded model are better than those obtained with the original model.

The present alternate implementation of solves the computational complexity associated with using large data (i.e. a larger tissue volume). It is also noted that the present expanded model performs better for the localization of the boundary dipoles than the original model.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A magnetocardiogram (MCG) system comprising:
   a sensor unit including an array of M×M electromagnetic MCG sensors producing a sparse measurement output of M×M data values, said sparse measurement output constituting a first MCG image, said first MCG image being a two-dimensional (2D) image having M×M picture elements (e.g. pixels);

a high resolution MCG image synthesizer for receiving said first MCG image and producing a higher resolution image representation of said first MCG image, said higher resolution image representation being a second MCG image of higher pixel density than said first MCG image, said second MCG image being a 2D image having P×P picture elements where P>M; and a de-noising image processing block for receiving said second MCG image and producing a de-noised lower resolution image representation of said second MCG image, said de-noised lower resolution image representation being a third 2D MCG image having M×M picture elements within a physical sensor area corresponding to the span of said M×M data values of said first MCG image, and said third MCG image having a reduced noise level as compared to said first MCG image.

2. The MCG system of claim 1, wherein said de-noising image processing block identifies as target picture elements the picture elements of said second MCG image whose image locations correspond to the image locations of the M×M data values of said first MCG image, and populates said physical sensor area with said target pictures elements.

3. The MCG system of claim 1, wherein the producing of said second MCG image by said high resolution MCG image synthesizer includes:

accessing a linear model defining a model MCG image of higher resolution than said first MCG image, said linear model establishing interpolation patterns between characteristics of the linear model and any data value of said sparse measurement output of M×M data values; and producing an intermediate MCG image by projecting said first MCG image onto the subspace of the linear model, and establishing coefficients for said intermediate MCG image in accordance with the linear model and said M×M data values.

4. The MCG system of claim 3, wherein said high resolution MCG image synthesizer outputs said intermediate image as said second MCG image, and each of said electromagnetic MCG sensors is a superconducting quantum interference device (SQUID).

5. The MCG system of claim 3, wherein said linear model is defined by creating a plurality of synthesized magnetocardiogram images having the same resolution as said second MCG image, said synthesized magnetocardiogram images being based on simulated electrical impulses within a three-dimensional spatial heart volume, as it would be perceived in an expected magnetocardiogram system.

6. The MCG system of claim 5, wherein said synthesized MCG images are based on randomly generated currents within said heart volume, and said linear model is created by using principal component analysis (PCA).

7. The MCG system of claim 3, wherein said interpolation patterns are established by the following steps:

(A) defining the following notation:
N×N dense Bz magnetic field map to form a vector;
M×M sparse measurement to form a vector;
K randomly generated single current dipoles Q;

(B) for each randomly generated current Q, computing an N×N magnetic field map using Biot-Savart equation and stack the resultant image to a vector $f_1$;

(C) repeating step (B) to obtain K samples and getting a data matrix $A=[f_1, f_2, \ldots f_K]$; and (D) training a PCA model given input data A, to obtain the eigenmatrix $\Sigma_f$.

8. The MCG system of claim 7, wherein said intermediate MCG image is created by:

given a new dipole and M×M sparse measurements $g_j$, finding the corresponding rows in the eigenmatrix, and denoting a resultant submatrix as $\Sigma_g$;

projecting the sparse measurement to the PCA subspace and computing the coefficients as $c_g=\Sigma_g^+(g_j-g_{mean})$, where $\Sigma_g^+$ is the pseudo inverse of $\Sigma_g$; and using the computed coefficients and original PCA space to reconstruct the dense magnetic field map Bz, as $f_j=\Sigma_f c_g + f_{mean}$.

9. The MCG system of claim 3, wherein said high resolution MCG image synthesizer includes an electric current localizer for determining a position and momentum of an electric current in accord with said intermediate MCG image, said electric current localizer evaluating the electromagnetic output data from each electromagnetic sensor in an x-y orientation (Bxy) assuming single dipole, computing dense Bxy from dense Bz, finding the image maximum in said intermediate MCG image, and using this determined position information as a starting point in an iterative process for identifying a three-dimensional position vector $\vec{p}$ and momentum vector $\vec{J}$ for said electric current; and said high resolution MCG image synthesizer uses the Biot-Sarvart Law for producing said second MCG image based on the identified three-dimensional position vector $\vec{p}$ and momentum vector $\vec{J}$.

10. The MCG system of claim 9, wherein the identifying of the three-dimensional position vector $\vec{p}$ and momentum vector $\vec{J}$ for said electric current further includes:

Given said third MCG image $B_z(i,j)(i=1,2,\ldots,N; j=1,2,\ldots,N)$, the maximal point of the tangential components $B'_{xy}(i,j)$ of $B_z(i,j)$ refers to the 2D position $(x_p,y_p)$ of the electric current, and the tangential components of $B_z(i,j)$ is computed as $B_{xy}(i,j)=\sqrt{(\partial B_z(i,j)/\partial x)^2+(\partial B_z(i,j)/\partial y)^2}$; and said iterative process for identifying position vector $\vec{p}$ and momentum vector $\vec{J}$ for said electric current includes:

(a) defining the Biot-Sarvart Law as $\vec{B}^m=\vec{J}\times\vec{R}_m=\vec{J}$ where $\vec{B}^m=\vec{B}(\vec{r}_m), \vec{J}=\vec{J}(\vec{p})$ and $$\vec{R}_m = \frac{\mu_0}{4\pi}\frac{(\vec{r}_m-\vec{p})}{\|(\vec{r}_m-\vec{p})\|^3};$$

(b) expanding this definition of the Biot-Sarvart Law to a matrix form by using a skew-symmetric matrix:

$$\vec{B}_m = -[\vec{R}_m]_\times \vec{J}$$
$$= -\begin{bmatrix} 0 & -R_m^3 & R_m^2 \\ R_m^3 & 0 & -R_m^1 \\ -R_m^2 & R_m^1 & 0 \end{bmatrix} \cdot \begin{bmatrix} J^1 \\ J^2 \\ J^3 \end{bmatrix}$$

where the z component of the magnetic field is computed as:

$$B_z^m = [R_m^2, -R_m^1] \cdot [J^1, J^2]'$$

where $R_m^1, R_m^2$ are x,y components of $\vec{R}_m$, and for said M×M electromagnetic sensors one has a linear system:

$$\begin{bmatrix} B_z^1 \\ B_z^2 \\ \vdots \\ B_z^M \end{bmatrix} = \begin{bmatrix} R_1^2 & -R_1^1 \\ R_2^2 & -R_2^1 \\ \vdots & \vdots \\ R_M^2 & -R_m^1 \end{bmatrix} \cdot \begin{bmatrix} J^1 \\ J^2 \end{bmatrix}$$

$$\underbrace{\phantom{xxx}}_{B} \quad \underbrace{\phantom{xxxxx}}_{R} \quad \underbrace{\phantom{x}}_{J}$$

where B is a measured M×1 vector, R is a M×2 position matrix that is computed from given $\vec{p}$ and $\vec{\delta}_m$, and a lease square solution for J provides an estimation of J defined as $J = (R^T R)^{-1} R^T B$;

(c) defining the Biot-Sarvart Law as $$\vec{B}^m = \frac{\mu_O}{4\pi} \frac{\vec{J} \times ((\vec{r}_O - \vec{\delta}_m) - \vec{p})}{\|(\vec{r}_O - \vec{\delta}_m) - \vec{p}\|^3} = \frac{\mu_O}{4\pi} \frac{\vec{J} \times ((\vec{\varepsilon}_O + \vec{\delta}_m) - \vec{p})}{\|\vec{\varepsilon}_O - \vec{\delta}_m\|^3}$$

letting $\alpha = 4\pi/\mu_0$ and $\vec{\varepsilon}_0 = \vec{r}_0 - \vec{p}$, identifying $\vec{\delta}_m$ as known for each sensor to redefining the Biot-Sarvart Law as $$\alpha \vec{B}^m = \frac{\vec{J} \times \vec{\varepsilon}_O + \vec{J} \times \vec{\delta}_m}{\|\vec{\varepsilon}_O - \vec{\delta}_m\|^3}$$

letting $\vec{\tau}_m = \vec{J} \times \vec{\delta}_m$ and $\vec{\delta}_0 = (x_\epsilon, y_\epsilon, z_\epsilon)^T$ and computing $\vec{\tau}_m$, from $\vec{J}$, for each sensor m=1:M, defining a nonlinear equation in terms of $(x_\epsilon, y_\epsilon, z_\epsilon)$ as $$\alpha B_z^m + \frac{-J^2 x_\varepsilon + J^1 y_\varepsilon + \tau_m^3}{((x_\varepsilon + \delta_m^1)^2 + (y_\varepsilon + \delta_m^2)^2 + (z_\varepsilon + \delta_m^3)^2)^{3/2}} = f^m(x_\varepsilon, y_\varepsilon, z_\varepsilon) = 0$$

letting $F = (f^1; f^2; \ldots; f^M) = 0$, and solving a least square solution of the nonlinear system F for $\vec{\varepsilon}_0$;

(d) using $\vec{\varepsilon}_0$ from step (c) to update the position matrix R and recompute J as in step (b), and iteratively repeating steps (b) and (c) until converges is achieved; and (e) defining the $\vec{p} = \vec{r}_0 - \vec{\varepsilon}_0$, and defining the initial depth z and magnitude $\|\vec{J}\|$ of the electric current as $$z = d/\sqrt{2.3} \text{ cm},$$

$$\|\vec{J}\| = \frac{4\pi d^2 B_z^{max}}{0.385 \mu_0}$$

where d is the distance between two magnetic poles in the third MCG image.

11. The MCG system of claim 1, wherein
said second MCG image spans an imaging area greater than said first MCG image.

12. The MCG system of claim 11, wherein:
said third MCG image spans an imaging area greater than said first MCG image;
the pixel density of the third MCG image's physical sensor area is uniformly extended throughout said third MCG image; and
the pixels of said third MCG image that lay beyond the physical sensor area are populated with simulated sensor data determined from said second MCG image.

13. The MCG system of claim 12, wherein said de-noising image processing block identifies as target pixels the picture elements of said second MCG image whose pixel image locations correspond to the pixel image locations of said third MCG image, and populates the pixel image locations of said third MCG with their corresponding target pictures elements.

14. The MCG system of claim 12, wherein the imaging span of said third MCG image is substantially the same as the imaging span of said second MCG image.

15. The MCG system of claim 11, wherein the producing of said higher resolution image representation of said first MCG image by said high resolution MCG image synthesizer includes:
accessing a linear model defining a model MCG image of substantially higher resolution than said first MCG image, said linear model being defined by creating a plurality of synthesized magnetocardiogram images having the same size and resolution as said second MCG image; said synthesized magnetocardiogram images being based on simulated electrical impulses within a three-dimensional spatial heart volume, as it would be perceived in a hypothetical magnetocardiogram system of similar resolution as said second MCG image; information from said plurality of synthesized magnetocardiogram images being incorporated into said linear model to establish interpolation patterns between characteristics of the linear model and any data value of said sparse measurement output; and
said producing of said second MCG image including the projecting said first MCG image onto the subspace of the linear model to establishing coefficients for use in the creation of said second MCG image.

16. The MCG system of claim 15, wherein said linear model is defined by:
(A) defining K simulated electrical impulse current dipoles Q;
(B) for each simulated electrical impulse Q, computing an N×N magnetic field map using Biot-Savart equation and stacking the resultant image to a vector $f_1$, so as to define a data matrix $A = [f_1, f_2, \ldots f_K]$ for the K simulated electrical impulses;
(C) defining a mean vector from said data matrix A of vectors; and
(D) defining a covariance matrix by determining the vector components needed for constructing the covariance matrix from said data matrix A, dividing said covariance matrix into L×L blocks, computing each of said L×L blocks separately by accessing into an active data memory only the vector components needed the L×L block being currently processed, storing the computed result for L×L block being currently processed, and combining the results of all L×L blocks.

17. A magnetocardiogram (MCG) system comprising:
a sensor unit including M×M electromagnetic sensors producing a sparse measurement output of M×M data values, said sparse measurement output constituting a first MCG image;
a high resolution MCG image synthesizer for receiving said first MCG image and producing a higher resolution image representation of said first MCG image, said higher resolution image representation being a second MCG image of higher pixel density than said first MCG image; and a de-noising image processing block for receiving said second MCG image and producing a de-noised lower resolution image representation of said second MCG image, de-noised lower resolution image representation being a third MCG image having M×M picture elements within a physical sensor area corresponding to the span of said M×M data values of said first MCG image and having a reduced noise level as compared to said first MCG image;

wherein the producing of said second MCG image by said high resolution MCG image synthesizer includes:

accessing a linear model defining a model MCG image of higher resolution than said first MCG image, said linear model establishing interpolation patterns between characteristics of the linear model and any data value of said sparse measurement output of M×M data values; and producing an intermediate MCG image by projecting said first MCG image onto the subspace of the linear model, and establishing coefficients for said intermediate MCG image in accordance with the linear model and said M×M data values; and wherein the producing of said intermediate MCG image includes:

defining the sparse measurement output as a vector g;
defining the linear model as $\Sigma$;
extracting from $\Sigma$ the row corresponding to sparse measurement output to form a sub-eigenmatrix $\Sigma_g$;
projecting g onto $\Sigma_g$;
defining the establishment of coefficients as $c_g = \Sigma_g^+ (g_i - \mu_g)$, where $\Sigma_g^+$ is the pseudo inverse of $\Sigma_g$, $\mu_g$ are extracted coefficients from a mean vector $\mu$ of linear model $\Sigma$; and
defining the intermediate MCG image vector h as $h = \Sigma \cdot c_g + \mu$.

18. A magnetocardiogram (MCG) system comprising:

a sensor unit including an array of M×M electromagnetic sensors producing a sparse measurement output of M×M data values, each of said electromagnetic sensors being a superconducting quantum interference device (SQUID), said sparse measurement output constituting a first MCG image, said first MCG image being a two-dimensional (2D) image having M×M picture elements (e.g. pixels), one per SQUID device;

a high resolution MCG image synthesizer for receiving said first MCG image and producing a higher resolution image representation of said first MCG image, said higher resolution image representation being a second MCG image of higher pixel density than said first MCG image said second MCG image being a 2D image being a 2D image having a P×P picture elements where P>M, said second MCG image being a 2D image spanning an imaging area greater than the image area of said first MCG image and encompassing the image area of said first MCG image.

19. The MCG system of claim 18, wherein the producing of said higher resolution image representation of said first MCG image by said high resolution MCG image synthesizer includes:

accessing a linear model defining a model MCG image of substantially higher resolution than said first MCG image, said linear model being defined by creating a plurality of synthesized magnetocardiogram images having a substantially similar size and resolution as said second MCG image; said synthesized magnetocardiogram images being based on simulated electrical impulses within a three-dimensional spatial volume as it would be perceived in a hypothetical magnetocardiogram system of similar resolution and image size as said second MCG image; information from said plurality of synthesized magnetocardiogram images being incorporated into said linear model to establish interpolation patterns between characteristics of the linear model and any data value of said sparse measurement output; and said producing of said second MCG image including the projecting said first MCG image onto the subspace of the linear model to establishing coefficients for said second MCG image.

20. The MCG system of claim 19, wherein:

said three-dimensional spatial volume is a simulated heart tissue volume;

said synthesized MCG images are based on randomly generated currents within said simulated heart tissue volume; and said linear model is created by using principal component analysis (PCA).

21. The MCG system of claim 19, wherein said linear model is defined by:

(A) defining K simulated electrical impulse current dipoles Q;

(B) for each simulated electrical impulse Q, computing an N×N magnetic field map using Biot-Savart equation and stacking the resultant image to a vector $f_1$, so as to define a data matrix $A = [f_1, f_2, \ldots]$ for the K simulated electrical impulses;

(C) defining a mean vector from said data matrix A of vectors; and (D) defining a covariance matrix by determining the vector components needed for constructing the covariance matrix from said data matrix A, dividing said covariance matrix into L×L blocks, computing each of said L×L blocks separately by accessing into an active data memory only the vector components needed the L×L block being currently processed, storing the computed result for L×L block being currently processed, and combining the results of all L×L blocks.

* * * * *